US010157267B2

(12) United States Patent
Mitchley

(10) Patent No.: US 10,157,267 B2
(45) Date of Patent: Dec. 18, 2018

(54) METHOD OF DETERMINING THE ATTENDANCE OF AN INDIVIDUAL AT A LOCATION AND A SYSTEM THEREFOR

(71) Applicant: Vitality Group International, Inc., Chicago, IL (US)

(72) Inventor: Stephen Ronald Mitchley, Chicago, IL (US)

(73) Assignee: Vitality Group International, Inc., Chicago, IL (US)

( * ) Notice: Subject to any disclaimer, the term of this patent is extended or adjusted under 35 U.S.C. 154(b) by 45 days.

(21) Appl. No.: 14/136,573

(22) Filed: Dec. 20, 2013

(65) Prior Publication Data

US 2014/0180710 A1 Jun. 26, 2014

Related U.S. Application Data

(60) Provisional application No. 61/740,540, filed on Dec. 21, 2012.

(51) Int. Cl.
*G06F 19/00* (2018.01)
*H04W 4/21* (2018.01)
*H04W 4/021* (2018.01)

(52) U.S. Cl.
CPC ...... *G06F 19/3481* (2013.01); *G06F 19/3418* (2013.01); *H04W 4/021* (2013.01); *H04W 4/21* (2018.02)

(58) Field of Classification Search
CPC .............................. G06Q 50/22; G06Q 50/24
(Continued)

(56) References Cited

U.S. PATENT DOCUMENTS 4,556,216 A 12/1985 Ptikanen
4,699,375 A 10/1987 Appelbaum et al.
(Continued)

FOREIGN PATENT DOCUMENTS

AU 2001/276596 3/2003
AU 2005/323847 2/2007
(Continued)

OTHER PUBLICATIONS

Office Action dated Dec. 11, 2014 for U.S. Appl. No. 13/782,203.
(Continued)

*Primary Examiner* — Eliza A Lam
(74) *Attorney, Agent, or Firm* — Fleit Gibbons Gutman Bongini & Bianco PL; Paul D. Bianco; Gary S. Winer

(57) ABSTRACT

A computer and mobile computing devices are used to determine participation in a health improvement plan. Data is stored pertaining to the identification of a members of the health improvement plan, as well as data pertaining to the identification of a mobile computing devices associated with the members. Additionally, data is stored pertaining to a set of locations each pertaining to a predetermined health improvement facility. As members use the health related facilities, information is received from a member's mobile computing device pertaining to a location of the mobile computing device within a predetermined distance with respect to a location within the set of locations. The time at which a location of the mobile computing device is within the predetermined distance, at a plurality of different times is stored, and then the stored time is analyzed to determine a level of participation of the member with the wellness program.

18 Claims, 6 Drawing Sheets

(58) Field of Classification Search
USPC .................................................. 705/2–3
See application file for complete search history.

(56) References Cited

U.S. PATENT DOCUMENTS

| | | | |
|---|---|---|---|
| 4,831,242 A | 5/1989 | Englehardt |
| 4,831,526 A | 5/1989 | Luchs et al. |
| 4,837,693 A | 6/1989 | Schotz |
| 4,860,275 A | 8/1989 | Kakinuma et al. |
| 4,975,840 A | 12/1990 | DeTore et al. |
| 5,062,645 A | 11/1991 | Goodman et al. |
| 5,136,502 A | 8/1992 | Van Remortel et al. |
| 5,297,026 A | 3/1994 | Hoffman |
| 5,301,105 A | 4/1994 | Cummings, Jr. |
| 5,324,077 A | 6/1994 | Kessler et al. |
| 5,429,506 A | 7/1995 | Brophy et al. |
| 5,490,260 A | 2/1996 | Miller et al. |
| 5,523,942 A | 6/1996 | Tyler et al. |
| 5,542,420 A | 8/1996 | Goldman et al. |
| 5,549,117 A | 8/1996 | Tacklind et al. |
| 5,550,734 A | 8/1996 | Tarter et al. |
| 5,574,803 A | 11/1996 | Gaborksi et al. |
| 5,630,073 A | 5/1997 | Nolan |
| 5,631,828 A | 5/1997 | Hagan |
| 5,655,085 A | 8/1997 | Ryan et al. |
| 5,655,997 A | 8/1997 | Greenberg et al. |
| 5,692,501 A | 12/1997 | Minturn |
| 5,722,418 A | 3/1998 | Bro |
| 5,745,893 A | 4/1998 | Hill et al. |
| 5,752,236 A | 5/1998 | Sexton et al. |
| 5,774,883 A | 6/1998 | Anderson et al. |
| 5,832,467 A | 11/1998 | Wavish |
| 5,867,821 A | 2/1999 | Ballantyne et al. |
| 5,890,129 A | 3/1999 | Spurgeon |
| 5,933,809 A | 8/1999 | Hunt et al. |
| 5,933,815 A | 8/1999 | Golden |
| 5,937,387 A | 8/1999 | Summerall et al. |
| 5,956,691 A | 9/1999 | Power |
| 5,987,434 A | 11/1999 | Libman |
| 5,991,744 A | 11/1999 | Dicrese |
| 6,018,730 A | 1/2000 | Nichols |
| 6,021,397 A | 2/2000 | Jones |
| 6,029,158 A | 2/2000 | Bertrand |
| 6,039,688 A | 3/2000 | Douglas et al. |
| 6,049,772 A | 4/2000 | Payne et al. |
| 6,085,174 A | 7/2000 | Edelman |
| 6,085,976 A | 7/2000 | Sehr |
| 6,088,686 A | 7/2000 | Walker |
| 6,108,641 A | 8/2000 | Kenna et al. |
| 6,112,986 A | 9/2000 | Berger et al. |
| 6,151,586 A | 11/2000 | Brown |
| 6,163,770 A | 12/2000 | Gamble |
| 6,198,996 B1 | 3/2001 | Berstis |
| 6,230,142 B1 | 5/2001 | Benigno et al. |
| 6,338,042 B1 | 1/2002 | Paizis |
| 6,385,589 B1 | 5/2002 | Trusheim et al. |
| 6,386,444 B1 | 5/2002 | Sullivan |
| 6,456,979 B1 | 9/2002 | Flagg |
| 6,513,532 B2 | 2/2003 | Mault et al. |
| 6,526,335 B1 | 2/2003 | Treyz et al. |
| 6,587,829 B1 | 7/2003 | Camarda et al. |
| 6,602,469 B1 | 8/2003 | Maus et al. |
| 6,611,815 B1 | 8/2003 | Lewis et al. |
| 6,915,211 B2 | 7/2005 | Kram et al. |
| 6,965,868 B1 | 11/2005 | Bednarek |
| 6,980,960 B2 | 12/2005 | Hajdukiewicz et al. |
| 7,156,665 B1 | 1/2007 | O'Connor |
| 7,165,044 B1 | 1/2007 | Chaffee |
| 7,194,444 B1 | 3/2007 | Nichols |
| 7,280,991 B1 | 10/2007 | Beams |
| 7,319,970 B1 | 1/2008 | Simone |
| 7,380,707 B1 | 6/2008 | Fredman |
| 7,383,223 B1 | 6/2008 | Dilip et al. |
| 7,392,210 B1 | 6/2008 | MacKay et al. |
| 7,386,524 B2 | 7/2008 | Hubbell |
| 7,398,217 B2 | 7/2008 | Lewis |
| 7,398,218 B1 | 7/2008 | Bernaski |
| 7,624,032 B2 | 11/2009 | Rabon |
| 7,624,059 B1 | 11/2009 | Jaffarian et al. |
| 7,630,937 B1 | 12/2009 | Mo et al. |
| 7,664,700 B1 | 2/2010 | Fisher |
| 7,672,756 B2 | 3/2010 | Breed |
| 7,672,857 B2 | 3/2010 | Padron et al. |
| 7,685,007 B1 | 3/2010 | Jacobson |
| 7,774,256 B1 | 8/2010 | Ryan et al. |
| 7,774,277 B1 | 8/2010 | Booker |
| 7,797,175 B2 | 9/2010 | Luedtke |
| 7,856,360 B2 * | 12/2010 | Kramer ............... G06Q 30/02 705/1.1 |
| 7,904,332 B1 | 3/2011 | Merkley |
| 7,908,156 B2 | 3/2011 | Gore et al. |
| 7,953,611 B2 | 5/2011 | Goodman et al. |
| 8,015,022 B2 | 9/2011 | Gore |
| 8,019,622 B2 * | 9/2011 | Kaboff ............... G06Q 10/00 342/357.25 |
| 8,086,523 B1 | 12/2011 | Palmer |
| 8,095,398 B2 | 1/2012 | Dellinger |
| 8,131,568 B2 | 3/2012 | Gore et al. |
| 8,131,570 B2 | 3/2012 | Levin et al. |
| 8,145,500 B2 | 3/2012 | Matisonn et al. |
| 8,151,916 B2 | 4/2012 | Gearhart |
| 8,185,449 B2 | 5/2012 | Ward |
| 8,185,463 B1 | 5/2012 | Ball |
| 8,190,455 B2 | 5/2012 | Gore et al. |
| 8,306,899 B2 | 11/2012 | Rabson et al. |
| 8,346,616 B2 | 1/2013 | Hwang |
| 8,359,208 B2 | 1/2013 | Slutzky et al. |
| 8,380,546 B2 | 2/2013 | Rabson et al. |
| 8,386,279 B2 | 2/2013 | Gore et al. |
| 8,438,046 B2 | 5/2013 | Mahaney et al. |
| 8,457,873 B2 | 6/2013 | Hyde et al. |
| 8,457,880 B1 | 6/2013 | Malalur et al. |
| 8,515,785 B2 | 8/2013 | Clark |
| 8,560,344 B2 * | 10/2013 | Earles ............... G06Q 30/02 705/2 |
| 8,598,977 B2 | 12/2013 | Maalouf et al. |
| 8,655,796 B2 * | 2/2014 | Udani ............... G06F 19/363 705/2 |
| 8,768,732 B2 | 7/2014 | Gore et al. |
| 9,661,480 B2 | 5/2017 | Ossin et al. |
| 2001/0018664 A1 | 8/2001 | Jacoves et al. |
| 2001/0037214 A1 | 11/2001 | Raskin et al. |
| 2001/0042785 A1 | 11/2001 | Walker et al. |
| 2001/0053984 A1 | 12/2001 | Joyce |
| 2002/0002495 A1 | 1/2002 | Ullman |
| 2002/0013717 A1 | 1/2002 | Ando et al. |
| 2002/0016923 A1 | 2/2002 | Knaus et al. |
| 2002/0029158 A1 | 3/2002 | Wolff et al. |
| 2002/0035486 A1 | 3/2002 | Huyn et al. |
| 2002/0038310 A1 | 3/2002 | Reitberg |
| 2002/0042763 A1 | 4/2002 | Pillay |
| 2002/0049617 A1 | 4/2002 | Lencki et al. |
| 2002/0052859 A1 | 5/2002 | Rosenfeld |
| 2002/0055859 A1 | 5/2002 | Goodman et al. |
| 2002/0087364 A1 | 7/2002 | Lerner et al. |
| 2002/0103677 A1 | 8/2002 | Sexton et al. |
| 2002/0103678 A1 | 8/2002 | Burkhalter et al. |
| 2002/0111827 A1 | 8/2002 | Levin et al. |
| 2002/0116231 A1 | 8/2002 | Hele et al. |
| 2002/0116266 A1 | 8/2002 | Marshall |
| 2002/0119434 A1 | 8/2002 | Beams |
| 2002/0120538 A1 | 8/2002 | Corrie et al. |
| 2002/0138309 A1 | 9/2002 | Thomas |
| 2002/0147617 A1 | 10/2002 | Schoenbaum |
| 2002/0152097 A1 | 10/2002 | Javors |
| 2002/0178033 A1 | 11/2002 | Yoshioka et al. |
| 2002/0184129 A1 | 12/2002 | Arena |
| 2002/0194120 A1 | 12/2002 | Russell |
| 2003/0009355 A1 | 1/2003 | Gupta |
| 2003/0023686 A1 | 1/2003 | Beams |
| 2003/0028483 A1 | 2/2003 | Sanders et al. |
| 2003/0033154 A1 | 2/2003 | Hajdukiewicz et al. |
| 2003/0055767 A1 | 3/2003 | Tamura et al. |
| 2003/0065561 A1 | 4/2003 | Brown |

(56) References Cited

U.S. PATENT DOCUMENTS

| | | |
|---|---|---|
| 2003/0065630 A1 | 4/2003 | Brown et al. |
| 2003/0078815 A1 | 4/2003 | Parsons |
| 2003/0084015 A1 | 5/2003 | Beams |
| 2003/0105652 A1 | 6/2003 | Arena |
| 2003/0120521 A1 | 6/2003 | Sherman |
| 2003/0120570 A1 | 6/2003 | Dellinger |
| 2003/0126054 A1 | 7/2003 | Purcell, Jr. |
| 2003/0135391 A1 | 7/2003 | Edmundson |
| 2003/0144888 A1 | 7/2003 | Baron |
| 2003/0149596 A1 | 8/2003 | Bost |
| 2003/0194071 A1 | 10/2003 | Ramian |
| 2003/0200101 A1 | 10/2003 | Adler |
| 2003/0200142 A1 | 10/2003 | Hicks et al. |
| 2003/0208385 A1 | 11/2003 | Zander |
| 2003/0212579 A1 | 11/2003 | Brown |
| 2003/0220834 A1 | 11/2003 | Leung et al. |
| 2003/0233278 A1 | 12/2003 | Marshall |
| 2004/0030625 A1 | 2/2004 | Rabson et al. |
| 2004/0039608 A1 | 2/2004 | Mazur |
| 2004/0039611 A1 | 2/2004 | Hong et al. |
| 2004/0059608 A1 | 3/2004 | Gore |
| 2004/0078594 A1* | 4/2004 | Scott .................. H04L 63/0428 726/35 |
| 2004/0088219 A1 | 5/2004 | Sanders et al. |
| 2004/0098279 A1 | 5/2004 | Frazier |
| 2004/0117302 A1 | 6/2004 | Weichert et al. |
| 2004/0138928 A1 | 7/2004 | Monk |
| 2004/0201460 A1 | 10/2004 | Bucholz et al. |
| 2004/0236605 A1 | 11/2004 | Somani |
| 2004/0238622 A1 | 12/2004 | Freiberg |
| 2004/0267570 A1 | 12/2004 | Becker et al. |
| 2004/0267579 A1 | 12/2004 | Markman |
| 2005/0010442 A1 | 1/2005 | Kragh |
| 2005/0010453 A1 | 1/2005 | Terlizzi |
| 2005/0010479 A1 | 1/2005 | Hannigan et al. |
| 2005/0033604 A1 | 2/2005 | Hogan |
| 2005/0033609 A1 | 2/2005 | Yang |
| 2005/0038679 A1 | 2/2005 | Short |
| 2005/0038681 A1 | 2/2005 | Covert |
| 2005/0055249 A1 | 3/2005 | Helitzer |
| 2005/0060209 A1 | 3/2005 | Hill |
| 2005/0071205 A1 | 3/2005 | Terlizzi |
| 2005/0102172 A1 | 5/2005 | Sirmans |
| 2005/0131742 A1 | 6/2005 | Hoffman et al. |
| 2005/0222867 A1 | 6/2005 | Underwood |
| 2005/0154618 A1 | 7/2005 | Kita |
| 2005/0216315 A1 | 9/2005 | Andersson |
| 2005/0222877 A1 | 10/2005 | Rabson et al. |
| 2005/0222878 A1 | 10/2005 | Rabson |
| 2005/0228692 A1 | 10/2005 | Hodgdon |
| 2005/0234742 A1 | 10/2005 | Hodgdon |
| 2005/0240449 A1 | 10/2005 | Rabson et al. |
| 2005/0256748 A1 | 11/2005 | Gore et al. |
| 2005/0267784 A1 | 12/2005 | Slen et al. |
| 2005/0279824 A1 | 12/2005 | Anderson et al. |
| 2005/0288971 A1 | 12/2005 | Cassandra |
| 2006/0041454 A1 | 2/2006 | Matisonn et al. |
| 2006/0041455 A1 | 2/2006 | Dehais |
| 2006/0049925 A1 | 3/2006 | Hara et al. |
| 2006/0053038 A1 | 3/2006 | Warren |
| 2006/0064320 A1 | 3/2006 | Postrel |
| 2006/0064331 A1 | 3/2006 | Odermott et al. |
| 2006/0069631 A1 | 3/2006 | Goulding et al. |
| 2006/0074801 A1 | 4/2006 | Pollard et al. |
| 2006/0089892 A1 | 4/2006 | Sullivan et al. |
| 2006/0116903 A1 | 6/2006 | Becerra |
| 2006/0129436 A1 | 6/2006 | Short |
| 2006/0143055 A1 | 6/2006 | Loy |
| 2006/0143056 A1 | 6/2006 | Taylor |
| 2006/0218011 A1 | 9/2006 | Walker et al. |
| 2006/0218023 A1 | 9/2006 | Conrad |
| 2006/0235782 A1 | 10/2006 | Oikonomidis |
| 2006/0287893 A1 | 12/2006 | Weiss |
| 2007/0027726 A1 | 2/2007 | Warren et al. |
| 2007/0050215 A1 | 3/2007 | Kil |
| 2007/0050217 A1 | 3/2007 | Holden |
| 2007/0055601 A1 | 3/2007 | Inderski |
| 2007/0061237 A1 | 3/2007 | Merton |
| 2007/0088488 A1 | 4/2007 | Reeves |
| 2007/0094053 A1 | 4/2007 | Samuels |
| 2007/0094125 A1 | 4/2007 | Izyayev |
| 2007/0106581 A1 | 5/2007 | Mitchell |
| 2007/0112669 A1 | 5/2007 | Snyder |
| 2007/0117302 A1 | 5/2007 | Jung |
| 2007/0122780 A1 | 5/2007 | Moon et al. |
| 2007/0136093 A1 | 6/2007 | Rankin |
| 2007/0203758 A1 | 8/2007 | Stephhens |
| 2007/0208681 A1 | 9/2007 | Nucholz |
| 2007/0233512 A1 | 10/2007 | Gore |
| 2008/0005016 A1 | 1/2008 | Uhlmann |
| 2008/0010095 A1 | 1/2008 | Joyce |
| 2008/0046382 A1 | 2/2008 | Metz |
| 2008/0059303 A1 | 3/2008 | Fordyce |
| 2008/0071600 A1 | 3/2008 | Johnson |
| 2008/0071661 A1 | 3/2008 | Jeudy et al. |
| 2008/0082369 A1 | 4/2008 | Carlson et al. |
| 2008/0082372 A1 | 4/2008 | Burch |
| 2008/0091471 A1 | 4/2008 | Michon |
| 2008/0109263 A1 | 5/2008 | Clark et al. |
| 2008/0147447 A1 | 6/2008 | Roche et al. |
| 2008/0154650 A1 | 6/2008 | Matisonn et al. |
| 2008/0172214 A1 | 7/2008 | Col |
| 2008/0189141 A1 | 8/2008 | Gore et al. |
| 2008/0189183 A1 | 8/2008 | Nicholson |
| 2008/0195486 A1 | 8/2008 | Sopinsky et al. |
| 2008/0197185 A1 | 8/2008 | Cronin et al. |
| 2008/0208769 A1 | 8/2008 | Beer et al. |
| 2008/0243558 A1 | 10/2008 | Gupte |
| 2008/0255979 A1 | 10/2008 | Slutzky et al. |
| 2008/0262877 A1 | 10/2008 | Hargroder |
| 2008/0262892 A1 | 10/2008 | Prager et al. |
| 2008/0288407 A1 | 11/2008 | Hamel et al. |
| 2008/0300923 A1 | 12/2008 | Theophilos |
| 2008/0312969 A1 | 12/2008 | Raines |
| 2009/0006140 A1 | 1/2009 | Wait |
| 2009/0024419 A1 | 1/2009 | McClellan et al. |
| 2009/0024478 A1 | 1/2009 | Dixon |
| 2009/0030736 A1 | 1/2009 | Tatro et al. |
| 2009/0030737 A1 | 1/2009 | Weiss |
| 2009/0037230 A1 | 2/2009 | Tracy |
| 2009/0055227 A1 | 2/2009 | Bakos |
| 2009/0076903 A1 | 3/2009 | Schwarzberg et al. |
| 2009/0105550 A1 | 4/2009 | Rothman |
| 2009/0150189 A1 | 6/2009 | Barron |
| 2009/0150192 A1 | 6/2009 | Gore |
| 2009/0164256 A1 | 6/2009 | Fisher |
| 2009/0179368 A1 | 7/2009 | Haimer |
| 2009/0198525 A1 | 8/2009 | Gore et al. |
| 2009/0204441 A1 | 8/2009 | Read |
| 2009/0204446 A1 | 8/2009 | Simon |
| 2009/0204447 A1 | 8/2009 | Tucher |
| 2009/0210257 A1 | 8/2009 | Chalfant |
| 2009/0240532 A1 | 9/2009 | Gore et al. |
| 2009/0259497 A1 | 10/2009 | Gore et al. |
| 2009/0265183 A1 | 10/2009 | Pollard et al. |
| 2009/0265191 A1 | 10/2009 | Evanitsky |
| 2009/0281840 A1 | 11/2009 | Hersch |
| 2009/0299773 A1 | 12/2009 | Gore et al. |
| 2009/0299774 A1 | 12/2009 | Gore et al. |
| 2009/0299775 A1 | 12/2009 | Gore et al. |
| 2009/0299776 A1 | 12/2009 | Gore et al. |
| 2009/0299844 A1 | 12/2009 | Reilly |
| 2009/0307015 A1 | 12/2009 | Gore et al. |
| 2010/0023354 A1 | 1/2010 | Gore et al. |
| 2010/0023384 A1 | 1/2010 | Pollard et al. |
| 2010/0030586 A1 | 2/2010 | Taylor |
| 2010/0049541 A1 | 2/2010 | Pollard et al. |
| 2010/0088112 A1 | 4/2010 | Krasny |
| 2010/0153296 A1 | 6/2010 | Volpert |
| 2010/0211403 A1 | 8/2010 | Allsup et al. |
| 2010/0228572 A1 | 9/2010 | Brooker |
| 2010/0332308 A1 | 12/2010 | Yap et al. |
| 2011/0021234 A1 | 1/2011 | Tibbits |
| 2011/0029182 A1 | 2/2011 | Hyde et al. |

(56) References Cited

U.S. PATENT DOCUMENTS

| | | |
|---|---|---|
| 2011/0029358 A1 | 2/2011 | Hyde et al. |
| 2011/0040579 A1 | 2/2011 | Havens |
| 2011/0060635 A1 | 3/2011 | Pollard et al. |
| 2011/0106370 A1 | 5/2011 | Duddle et al. |
| 2011/0112872 A1 | 5/2011 | Rabson et al. |
| 2011/0119093 A1 | 5/2011 | Rabson |
| 2011/0137687 A1 | 6/2011 | Duddle |
| 2011/0161116 A1 | 6/2011 | Peak et al. |
| 2011/0161255 A1 | 6/2011 | Short |
| 2011/0208671 A1 | 8/2011 | Edwards |
| 2011/0306028 A1 | 12/2011 | Galimore |
| 2012/0036050 A1 | 2/2012 | Norris |
| 2012/0065805 A1 | 3/2012 | Montalvo |
| 2012/0078761 A1 | 3/2012 | Holland et al. |
| 2012/0089442 A1 | 4/2012 | Olsson et al. |
| 2012/0109417 A1 | 5/2012 | Berkobin et al. |
| 2012/0130727 A1 | 5/2012 | Ahmed |
| 2012/0185282 A1 | 7/2012 | Gore et al. |
| 2012/0191469 A1 | 7/2012 | Akradi |
| 2012/0203713 A1 | 8/2012 | Mayers et al. |
| 2012/0226421 A1 | 9/2012 | Kote et al. |
| 2012/0245839 A1 | 9/2012 | Syed et al. |
| 2012/0245992 A1 | 9/2012 | Pender et al. |
| 2012/0251993 A1 | 10/2012 | Chidambaran et al. |
| 2012/0271699 A1 | 10/2012 | Ross et al. |
| 2012/0278211 A1* | 11/2012 | Loveland ............. G07C 1/10 705/32 |
| 2012/0330687 A1 | 12/2012 | Hilario et al. |
| 2013/0013344 A1 | 1/2013 | Ernstberger et al. |
| 2013/0013348 A1 | 1/2013 | Ling et al. |
| 2013/0041585 A1 | 2/2013 | Czompo et al. |
| 2013/0054431 A1 | 2/2013 | Forman |
| 2013/0060583 A1 | 3/2013 | Collins et al. |
| 2013/0085787 A1 | 4/2013 | Gore |
| 2013/0085819 A1 | 4/2013 | Gore et al. |
| 2013/0090955 A1 | 4/2013 | Gore et al. |
| 2013/0175769 A1 | 7/2013 | Yang |
| 2013/0179198 A1 | 7/2013 | Maruko |
| 2013/0231963 A1 | 9/2013 | Gore et al. |
| 2013/0260344 A1 | 10/2013 | Musicant |
| 2013/0282472 A1 | 10/2013 | Penilla et al. |
| 2013/0311250 A1 | 11/2013 | Hickethier et al. |
| 2013/0317860 A1 | 11/2013 | Schumann, Jr. |
| 2013/0318008 A1 | 11/2013 | Gore |
| 2014/0025454 A1 | 1/2014 | Das et al. |
| 2014/0108115 A1* | 4/2014 | White ............. G06Q 30/0217 705/14.19 |
| 2014/0274016 A1 | 9/2014 | Timm et al. |
| 2014/0278580 A1 | 9/2014 | Brown et al. |
| 2014/0309844 A1 | 10/2014 | Breed |
| 2014/0337204 A1 | 11/2014 | Noach et al. |
| 2014/0358746 A1 | 12/2014 | Segal et al. |
| 2014/0372152 A1 | 12/2014 | Noach et al. |
| 2015/0081329 A1 | 3/2015 | Saidal et al. |
| 2015/0091713 A1 | 4/2015 | Kohlenberg et al. |
| 2015/0203072 A1 | 7/2015 | Hockman |
| 2015/0235006 A1 | 8/2015 | Nichols |
| 2015/0235562 A1 | 8/2015 | Klein |

FOREIGN PATENT DOCUMENTS

| | | |
|---|---|---|
| AU | 2007/257457 | 1/2009 |
| AU | 2007/257458 | 1/2009 |
| AU | 2007/257546 | 1/2009 |
| AU | 2007/298514 | 2/2009 |
| AU | 2007/301521 | 5/2009 |
| CN | 2005/880047059 | 7/2007 |
| EP | 1050821 | 11/2000 |
| EP | 2412588 | 2/2012 |
| IL | 195735 | 12/2008 |
| IL | 195737 | 12/2008 |
| IL | 195738 | 12/2008 |
| WO | 01/71372 | 9/2001 |
| WO | 02/047074 | 6/2002 |
| WO | 03/007230 | 1/2003 |
| WO | 07/141695 | 12/2007 |
| WO | 07/141696 | 12/2007 |
| WO | 07/141968 | 12/2007 |
| WO | 08/035280 | 3/2008 |
| WO | 2008/050136 | 5/2008 |
| WO | 2012/085691 | 6/2012 |
| WO | 2010085691 | 6/2012 |
| WO | 2013/084113 | 6/2013 |
| WO | 2013084111 | 6/2013 |
| WO | 2013084118 | 6/2013 |
| WO | 2014/113431 | 1/2014 |
| WO | 2017-046727 A1 | 3/2017 |
| WO | 2017/051309 A1 | 3/2017 |
| ZA | 98/02005 | 3/1998 |
| ZA | 99/1746 | 3/1998 |
| ZA | 98/11943 | 12/1998 |
| ZA | 2000/04682 | 9/2000 |
| ZA | 2004/02587 | 4/2004 |
| ZA | 2004/02891 | 4/2004 |
| ZA | 2004/05935 | 7/2004 |
| ZA | 2004/06294 | 8/2004 |
| ZA | 2006/01934 | 3/2006 |
| ZA | 2006/04673 | 6/2006 |
| ZA | 2006/04674 | 6/2006 |
| ZA | 2006/04687 | 6/2006 |
| ZA | 2006/04688 | 6/2006 |
| ZA | 2006/07789 | 9/2006 |
| ZA | 2006/07992 | 9/2006 |
| ZA | 2008-03529 | 4/2008 |
| ZA | 2008/04807 | 6/2008 |
| ZA | 2008/04808 | 6/2008 |
| ZA | 2008/04809 | 6/2008 |
| ZA | 2008/04810 | 6/2008 |
| ZA | 2008/04811 | 6/2008 |
| ZA | 2009/01740 | 3/2009 |
| ZA | 2010/09180 | 12/2010 |
| ZA | 2011/00938 | 2/2011 |
| ZA | 2011/07402 | 10/2011 |
| ZA | 2012/01595 | 3/2012 |
| ZA | 2012/05316 | 7/2012 |

OTHER PUBLICATIONS

Response filed May 11, 2015 to Office Action dated Dec. 11, 2014 for U.S. Appl. No. 13/782,203.
Response filed May 20, 2015 to Office Action dated Nov. 20, 2014 for U.S. Appl. No. 12/477,225.
U.S. Appl. No. 12/303,395, Non Final Office Action dated Nov. 6, 2014.
Office Action dated Sep. 26, 2016 for U.S. Appl. No. 12/33,465.
Office Action dated Sep. 27, 2016 for U.S. Appl. No. 11/794,830.
Final Office Action dated Sep. 26, 2016 for U.S. Appl. No. 13/641,145.
Final Office Action dated Sep. 29, 2016 for U.S. Appl. No. 14/364,004.
Office Action dated Oct. 4, 2016 for U.S. Appl. No. 13/648,309.
Andrew Cohen; Putting Wellness to work; date Mar. 1, 1997; Athletic Business, pp. 1-7.
www.netpulse.net; Netpulsue Makes Working Out More than a Calorie-Burning Session; date Mar. 21, 1998, pp. 1-2.
www.netpulse.net; 24 Hour Fitness Partners with Netpulse; date Mar. 9, 1998; p. 1.
Trends in Medical Benefit Plan Design to Control Claim Costs; Record of Society of Actuaries; date 1982; vol. 8, No. 2, pp. 515-531.
David Richards, Return of Premium Disability Insurance; The Black Hole, dated Jul. 15, 2010, p. 1-4.
"Sidelines" WWD, p. 10—STIC Scientific and Technical Information Center, Feb. 3, 2000.
Co-pending U.S. Appl. No. 11/074,453, Final Office Action dated Jun. 19, 2010.
Co-pending U.S. Appl. No. 11/189,647, Request for Continued Examination filed Jul. 19, 2010.
Co-pending U.S. Appl. No. 11/715,181, Response filed Aug. 12, 2010.
Co-pending U.S. Appl. No. 12/112,165, Non-final Office Action dated Sep. 2, 2010.

(56) References Cited

OTHER PUBLICATIONS

Co-pending U.S. Appl. No. 10/251,120, Request for Continued Examination filed Oct. 6, 2010.
Co-pending U.S. Appl. No. 12/303,391, Non final Office Action dated Nov. 24, 2010.
Co-pending U.S. Appl. No. 11/074,453, Response to final office action dated Dec. 20, 2010.
Co-pending U.S. Appl. No. 09/876,311, Non-final Office Action dated Jul. 9, 2010.
Written Opinion dated Dec. 28, 2016 for PCT/IB16/55602.
International Search Report dated Dec. 28, 2016 for PCT/IB16/55602.
Office Action dated Jan. 15, 2016 for U.S. Appl. No. 14/363,890.
Office Action dated Feb. 3, 2016 for U.S. Appl. No. 14/364,004.
Office Action dated Feb. 4, 2016 for U.S. Appl. No. 13/386,431.
Response to Final Office Action and Notice of Appeal filed Feb. 9, 2016 for U.S. Appl. No. 12/333,465.
Response to Office Action filed Feb. 12, 2016 for U.S. Appl. No. 14/415,296.
Response to Office Action filed Feb. 22, 2016 for U.S. Appl. No. 13/996,058.
Final Office Action dated Feb. 23, 2016 for U.S. Appl. No. 11/794,830.
Response filed May 1, 2017 for U.S. Appl. No. 13/996,058.
Final office action dated Aug. 15, 2017 for U.S. Appl. No. 13/996,058.
Office Action dated Aug. 9, 2017 for U.S. Appl. No. 13/641,145.
RCE Response filed Aug. 24, 2017 for U.S. Appl. No. 12/333,465.
Supplemental Response filed Aug. 29, 2017 for U.S. Appl. No. 12/333,465.
U.S. Appl. No. 13/641,143, Final Office Action dated Oct. 21, 2014.
U.S. Appl. No. 13/641,155, Final Office Action dated Oct. 21, 2014.
RCE Response filed Apr. 9, 2018 for U.S. Appl. No. 13/996,058.
Response filed Apr. 9, 2018 for U.S. Appl. No. 13/641,145.
Office Action dated Dec. 19, 2011 for U.S. Appl. No. 11/794,830.
Notice of Non-Compliant Amendment dated Apr. 18, 2012 for U.S. Appl. No. 11/794,830.
Supplemental Response filed May 18, 2012 to Notice of Non-Compliant Amendment dated Apr. 18, 2012 for U.S. Appl. No. 11/794,830.
Response to Office Action filed Nov. 25, 2015 for U.S. Appl. No. 11/097,947.
Final Office Action dated Feb. 12, 2014 for U.S. Appl. No. 12/477,225.
Response filed Nov. 20, 2015 to Office Action dated Jun. 3, 2015 for U.S. Appl. No. 11/794,830.
Response filed Nov. 30, 2015 to final Office Action dated Jul. 1, 2015 for U.S. Appl. No. 13/648,309.
Response filed Dec. 1, 2015 to final Office Action dated Jul. 6, 2015 for U.S. Appl. No. 12/477,225.
Response filed Dec. 3, 2015 to Office Action dated Jul. 9, 2015 for U.S. Appl. No. 14/363,890.
Response filed Jun. 27, 2011 to Office Action dated Mar. 25, 2011 for U.S. Appl. No. 12/477,225.
Office Action dated Jul. 17, 2012 for U.S. Appl. No. 12/477,225.
Response filed Nov. 19, 2012 to Office Action dated Jul. 17, 2012 for U.S. Appl. No. 12/477,225.
Response filed May 6, 2013 to final Office Action dated Feb. 4, 2013 for U.S. Appl. No. 12/477,225.
Office Action dated Sep. 9, 2013 for U.S. Appl. No. 12/477,225.
Response filed Dec. 9, 2013 to Office Action dated Sep. 9, 2013 for U.S. Appl. No. 12/477,225.
International Search Report dated Dec. 15, 2016 for PCT/IB2016/055489.
Written Opinion dated Dec. 15, 2016 for PCT/IB2016/055489.
Response to Office Action filed Mar. 27, 2017 for U.S. Appl. No. 11/794,830.
Response to Office Action filed Mar. 27, 2017 for U.S. Appl. No. 13/641,145.
Response to Office Action filed Mar. 27, 2017 for U.S. Appl. No. 14/363,890.
Response to Office Action filed Mar. 29, 2017 for U.S. Appl. No. 14/364,004.
Final Office Action dated Mar. 24, 2017 for U.S. Appl. No. 12/333,465.
Gore, The case for Consumer Engagement in the funding of Healthcare IAAHS 2007.
Preferred Health Systems—Preferred News—vol. 9, issue 1, Spring 2008.
Discovery Why Discovery Life May 29, 2008.
BX Link Your Company Websites Discovery Life Plans Jan. 13, 2003.
Destiny Health Individual Brochure Health Coverage modified Oct. 18, 2006.
DaSilva Roseanne The Impact of Wellness Activities on Hospital Claims Experience, Joint Colloquium of the IACA, PBSS and IAAHS May 2008 Oct. 1, 2004.
M. Doty et al., Issue Brief, Maintaining Health Insurance During a Recession, 6 pgs, 2001.
R. Merhr, ARIA—The Concept of the Level-Premium Whole Life Insurance Policy, The Journal of Risk and Insurance, vol. 42, No. 3 (Sep. 1975) pp. 419-431.
STIC Search Report EIC 3600, Scientific and Technical Information Center, 63 pgs.
Web-site Google Search Google Employee Wellness Payment dated Feb. 12, 2012.
Wellness Source—How Much Does a Good Wellness Program Cost? 2 pgs.
South African Patent Journal No. 6 of 1, Jun. 2099, vol. 42, p. 229.
South African Patent Application 2008/04810 filed Jun. 26, 2009— Annotated with Paragragh numbers.
South African Patents Act, No. 57 of 1978 as amended by Patents Amendment Act No. 58 of 2002.
Discovery Life, "Technical guide for financial advisers" Nov. 11, 2009.
Web-site www.MarketGuard.com—"Guard your Mortgage Payments Against Rate Rise" pp. 32 ~, dated Nov. 14, 2012.
Insurance Benefits / Coverage outline, dated 2006.
U.S. Appl. No. 09/876,311, Response to Office Action dated Feb. 5, 2009.
U.S. Appl. No. 09/876,311, Response to Office Action dated May 28, 2009.
U.S. Appl. No. 09/876,311, Response to Office Action dated Sep. 10, 2009.
U.S. Appl. No. 09/876,311, Response to Office Action dated May 17, 2010.
U.S. Appl. No. 09/982,274, filed Oct. 17, 2001.
U.S. Appl. No. 09/982,274, Final Rejection dated Nov. 27, 2006.
U.S. Appl. No. 09/982,274, Final Rejection dated May 6, 2008.
U.S. Appl. No. 09/982,274, Final Rejection dated Jun. 9, 2009.
U.S. Appl. No. 09/982,274, Non-Final Rejection dated Mar. 3, 2006.
U.S. Appl. No. 09/982,274, Non-Final Rejection dated Aug. 9, 2007.
U.S. Appl. No. 09/982,274, Non-Final Rejection dated Oct. 17, 2008.
U.S. Appl. No. 09/982,274, Response to Office Action dated Sep. 6, 2006.
U.S. Appl. No. 09/982,274, Response to Office Action dated May 29, 2007.
U.S. Appl. No. 09/982,274, Response to Office Action dated Jan. 22, 2008.
U.S. Appl. No. 09/982,274, Response to Office Action dated Aug. 6, 2008.
U.S. Appl. No. 09/982,274, Response to Office Action dated Feb. 17, 2009.
U.S. Appl. No. 09/982,274, Notice of Appeal filed Sep. 9, 2009.
U.S. Appl. No. 09/982,274, Appeal Brief Filed Nov. 9, 2009.
U.S. Appl. No. 09/982,274, Reply Brief filed Apr. 2, 2010.
U.S. Appl. No. 12/112,165, filed Apr. 30, 2001.
U.S. Appl. No. 10/251,120, filed Sep. 20, 2002.
U.S. Appl. No. 10/251,120, Final Rejection dated Dec. 31, 2007.
U.S. Appl. No. 10/251,120, Final Rejection dated Jun. 25, 2009.
U.S. Appl. No. 10/251,120, Non-Final Rejection dated Mar. 29, 2007.
U.S. Appl. No. 10/251,120, Non-Final Rejection dated Jan. 5, 2009.

(56) References Cited

OTHER PUBLICATIONS

U.S. Appl. No. 10/251,120, Examiner Summary dated Oct. 21, 2009.
U.S. Appl. No. 10/251,120, Examiner Summary dated Jul. 6, 2010.
U.S. Appl. No. 10/251,120, Response to Office Action dated Sep. 28, 2007.
U.S. Appl. No. 10/251,120, Response to Office Action dated Oct. 7, 2008.
U.S. Appl. No. 10/251,120, Response to Office Action dated Apr. 6, 2009.
U.S. Appl. No. 10/251,120, Appeal Brief Filed Mar. 24, 2010.
U.S. Appl. No. 12/122,549, filed May 16, 2008.
U.S. Appl. No. 11/198,206, filed Aug. 5, 2005.
U.S. Appl. No. 11/198,206, Final Rejection dated Jan. 23, 2009.
U.S. Appl. No. 11/198,206, Non-Final Rejection dated Jun. 30, 2008.
U.S. Appl. No. 11/198,206, Response to Office Action dated Oct. 30, 2008.
U.S. Appl. No. 12/333,465, filed Dec. 12, 2008.
U.S. Appl. No. 12/262,266, filed Oct. 31, 2008.
U.S. Appl. No. 12/303,388, filed Dec. 4, 2008.
U.S. Appl. No. 12/303,391, filed Dec. 4, 2008.
U.S. Appl. No. 12/303,395, filed Dec. 4, 200.
U.S. Appl. No. 12/303,399, filed Dec. 4, 2008.
U.S. Appl. No. 12/441,447, filed Mar. 16, 2009.
U.S. Appl. No. 10/344,176, filed Aug. 15, 2003.
U.S. Appl. No. 10/344,176, Final Rejection dated Oct. 30, 2008.
U.S. Appl. No. 10/344,176, Final Rejection dated Mar. 2, 2010.
U.S. Appl. No. 10/344,176, Non-Final Rejection dated Dec. 19, 2007.
U.S. Appl. No. 10/344,176, Non-Final Rejection dated Jun. 8, 2009.
U.S. Appl. No. 10/344,176, Response to Office Action dated May 19, 2008.
U.S. Appl. No. 10/344,176, Response to Office Action dated Mar. 2, 2009.
U.S. Appl. No. 14/415,296, filed Jan. 16, 2015.
Final Office Action dated Jul. 1, 2015 for U.S. Appl. No. 13/648,309.
U.S. Appl. No. 13/832,456, filed Mar. 15, 2013.
International Search Report dated Aug. 26, 2014 for PCT/2014/030174.
Final Office Action dated Jul. 6, 2015 for U.S. Appl. No. 12/477,225.
International Preliminary Report on Patentability dated Jun. 30, 2015 for PCT/IB2012/056783 filed Nov. 28, 2012.
Written Opinion of the International Searching Authority dated May 9, 2013 for PCT/IB2012/056783 filed Nov. 28, 2012.
International Search Report dated May 9, 2013 for PCT/IB2012/056783 filed Nov. 28, 2012.
Office Action dated Jul. 9, 2015 for U.S. Appl. No. 14/363,890.
Response filed Jul. 25, 2011 to Office Action dated May 23, 2011 for U.S. Appl. No. 11/074,453.
Final Office Action dated Aug. 16, 2012 for U.S. Appl. No. 11/074,453.
Response filed Nov. 16, 2012 to Final Office Action dated Aug. 16, 2012 for U.S. Appl. No. 11/074,453.
Appeal Brief filed May 15, 2013 to Final Office Action dated Aug. 16, 2012 for U.S. Appl. No. 11/074,453.
Amended Appeal Brief filed Jun. 18, 2013 to Final Office Action dated Aug. 16, 2012 for U.S. Appl. No. 11/074,453.
Office Action dated Jul. 8, 2015 for U.S. Appl. No. 11/074,453.
Office Action dated Aug. 12, 2015 for U.S. Appl. No. 14/415,286.
Final Office Action dated Aug. 10, 2015 for U.S. Appl. No. 12/333,465.
U.S. Appl. No. 13/782,203, filed Mar. 1, 2013.
Final Office Action dated Aug. 21, 2015 for U.S. Appl. No. 13/996,058.
Response filed Sep. 8, 2015 to Office Action dated Apr. 8, 2015 for U.S. Appl. No. 13/365,566.
Office Action dated Nov. 5, 2012 for U.S. Appl. No. 13/365,566.
Response filed Mar. 5, 2013 to Office Action dated Nov. 5, 2012 for U.S. Appl. No. 13/365,566.
Office Action dated Aug. 15, 2014 for U.S. Appl. No. 13/365,566.
Response filed Oct. 21, 2013 to Office Action dated Aug. 15, 2014 for U.S. Appl. No. 13/365,566.
Office Action dated Feb. 24, 2014 for U.S. Appl. No. 13/365,566.
Response filed Jul. 23, 2014 to Office Action dated Feb. 24, 2014 for U.S. Appl. No. 13/365,566.
Discovery Life "The Discovery life Portfolio", 62 pgs—2008.
AFLAC "Personal Disability Income Protector", 6 pgs—Jul. 2003.
R.C. Olmstead, "Our Products" May 2008.
Discovery Life—"Why Discovery Life"—4 pgs—May 29, 2008.
GE Group Life Assurance Company—Group Short Term Disability Insurance—18 pgs, Oct. 29, 2004.
Wenfin Financial Services, "Discovery Life Plan" www.bmlink.co.za/WenFininsurance—Website download, 58 pgs, Aug. 5, 2011.
EconEdLink—"How Long is Your life?"—Tutorial from EconEdLink.com web-site, 4 pgs, posted Sep. 13, 2004.
AFLAC—"Personal Cancer Indemnity Plan" Level 3, 11 pgs, Jun. 2005.
Gendell Murray, "Retirement age Declines again in 1990s", Monthly Labor Review, 10 pgs, Oct. 2001.
Discovery Life "Benefit version Reference Guide" Oct. 2008.
Discovery Life—"Discovery life Group Risk Life Plan".
WenfinWebPages for Discovery Life Nov. 13, 2006.
AFLAC—Discovery Life "Application for Discovery Card Protector" Nov. 2007.
Discovery Life "The Disovery Life Portfolio" Nov. 20, 2008.
Discovery Life "Discovery Individual Lie Plan Guide" Aug. 4, 2009
EconEdLink—How Long is Your life?—Tutorial from EconEdLink.com web-site, posted Sep. 13, 2004.
Discovery Life "The Discovery Life Portfolio" Jun. 2008.
Discovery Invest Group Retirement {Plan Financial Solutions for employees: Oct. 17, 2009.
ATG Customer Success Story: Discovery Heathly 2006 ART Tech Group, Inc.
Discovery Vitality; Discovery Vitality 2009 Sep. 12, 2008.
Discovery Invest, Group Retirement Plan Finanical solutions for employees Jan. 17, 2009.
Baker et al. Pay for Performance Incentive Programs in Healthcare; Market Dynammics and Business Process-Research Report 2003.
PruHealth, Individual Policy Document Jul. 2008.
Discovery Vitality, Lesson Plans Grade 4 nad 5 Apr. 2, 2008.
HLC Financial Services, Discovery News Feb. 2009.
The Discovery Life, "Technical guide for financial advisers" Nov. 2008.
Rintelman, Mary Jane, "Choice and cost-savings", Credit Union Management, vol. 19, No. 7, pp. 48, 50. Jul. 1996.
Woodard, Kathy, "Stay healthy for real fun—and profit", Business First Columbus, vol. 12, No. 19, S.1, p. 13. Jan. 1996.
Spencer, Peter L., "New plan cuts health car costs in half (advantage of health care plan with high deductible)", Consumers' Research Magazine, vol. 76, No. 10, pp. 16. Oct. 1993.
Commununity Hearth Health Programs: Components, Ratio: John P. Elder, Thomas L. Schmid, Phyillis Dower and Sonja Hedlund; Journal of Public Health Policy; Palgrave Macmillian; 1993 winter; pp. 463-479.
Ferling ("New plans, New policies," Ferling, Rhona. Best's Review; Apr. 1993 p. 78).
"Plan Highlights for El Paso ISD" Salary Protection Insurance Plan, web-site—http://w3.unumprovident.com/enroll/elpasoisd/your_plan.htm, Mar. 3, 2008.
Consumer-Driven Health Plans Catch on as Myths Fall by Wayside (Sep. 4). PR Newswire, 1.
Art Technology Group; Discovery Holdings to exploit online interest in healthcare and life assurance with ATG commerce functionality; Revenue potential significant as 70% of Discovery members access the internet. (Oct. 28). M2 Presswire, 1.
"Absenteeism Control"; Cole, Thomas C. et al; Management Decision; London: 1992. vol. 20, Iss. 2; p. 12 (AC).
Saleem, Haneefa: "Health Spending Accounts"; Dec. 19, 2003; posted online at http://www.bls.gov/opub/cwc/print/cm20031022ar01p1.htm.
Insure.com; "The lowdown on life insurance medical exams"; Jun. 28, 2006; Imaged from the Internet Archive Waybackmachine on

(56) References Cited

OTHER PUBLICATIONS

May 10, 2006 at http://web.archive.org/web/20060628231712/http://articles.moneycentral.msn.com/Insurance/Insureyourlife/thelowdownonlifeinsurancwemedicalexams.aspx.
Definition of insurance, New Penguin Business Dictionary, Retreieved Oct. 26, 2008 from http://www.credoreference.com/entry/6892512/.
Web-site Google Search—Google Employee Wellness Payment—2 pgs, dated Feb. 12, 2012.
Final Office Action dated Sep. 23, 2015 for U.S. Appl. No. 13/365,566.
Response filed Oct. 5, 2015 for Final Office Action dated May 4, 2015 for U.S. Appl. No. 13/641,145.
International Search Report dated Sep. 2, 2011 for PCT/IB2011/051603.
Written Opinion of the International Searching Authority dated Sep. 14, 2011 for PCT/IB2011/051603.
International Preliminary Report on Patentability dated Oct. 16, 2012 for PCT/IB2011/051603.
Office Action dated Sep. 27, 2013 for U.S. Appl. No. 13/648,309, filed Oct. 10, 2012.
Response filed Dec. 20, 2013 to Office Action dated Sep. 27, 2013 for U.S. Appl. No. 13/648,309.
Final Office Action dated Apr. 23, 2014 for U.S. Appl. No. 13/648,309.
Notice of Appeal and Response filed Jul. 23, 2014 to Final Office Action dated Apr. 23, 2014 for U.S. Appl. No. 13/648,309.
Office Action dated Oct. 7, 2014 for U.S. Appl. No. 13/648,309.
Response dated Mar. 9, 2015 for Office Action dated Oct. 7, 2014 for U.S. Appl. No. 13/648,309.
Final Office Action dated Apr. 20, 2016 for U.S. Appl. No. 11/074,453.
Office Action dated Mar. 14, 2016 for U.S. Appl. No. 12/477,225.
Response filed Jun. 2, 2016 for U.S. Appl. No. 11/097,947.
International Search Report PCT/IB11/52875 dated Nov. 23, 2011.
Connell Medical Tourism: Sea, sun, sand and surgery, Dec. 2006, Tourism Management, vol. 27, issue 6, pp. 1093-110.
U.S. Appl. No. 12/912,009 Response filed Aug. 8, 2013.
U.S. Appl. No. 13/318,620,Final Office Action dated Sep. 3, 2013.
U.S. Appl. No. 13/782,203, Non-final Office Action dated Sep. 5, 2013.
Response filed Jul. 14, 2014 to Office Action dated Feb. 12, 2014 for U.S. Appl. No. 12/477,225.
Response filed Feb. 5, 2014 to Office Action dated Sep. 5, 2013 for U.S. Appl. No. 13/782,203.
Response filed Sep. 16, 2014 to Office Action dated Apr. 16, 2014 for U.S. Appl. No. 13/782,203.
Office Action dated Jun. 3, 2015 for U.S. Appl. No. 11/794,830.
Response filed Apr. 16, 2012 for Office Action dated Dec. 19, 2011 for U.S. Appl. No. 11/794,830.
Final Office Action dated Oct. 1, 2012 for U.S. Appl. No. 11/794,830.
Response filed Dec. 31, 2012 to Office Action dated Oct. 1, 2012 for U.S. Appl. No. 11/794,830.
Office Action dated Dec. 13, 2013 for U.S. Appl. No. 11/794,830.
Responde filed Mar. 14, 2014 to Office Action dated Dec. 13, 2013 for U.S. Appl. No. 11/794,830.
Response filed Nov. 24, 2014 to Office Action dated Jun. 24, 2014 for U.S. Appl. No. 11/794,830.
Response filed Aug. 28, 2013 to Office Action dated Mar. 28, 2013 for U.S. Appl. No. 13/386,431.
Final Office Action dated Nov. 15, 2013 for U.S. Appl. No. 13/386,431.
Appeal Brief filed May 19, 2014 for U.S. Appl. No. 13/386,431.
Appeal Brief filed Jun. 11, 2014 for U.S. Appl. No. 13/386,431.
Examiner answer dated Sep. 19, 2014 to appeal brief filed May 19, 2014 and Jun. 11, 2014 from the Office Action dated Nov. 15, 2013 for U.S. Appl. No. 13/386,431.
Office Action dated Jan. 29, 2015 for U.S. Appl. No. 13/386,431.
Response filed Jun. 29, 2015 to Office Action dated Jan. 29, 2015 for U.S. Appl. No. 13/386,431.
Restriction Requirement dated Apr. 23, 2015 for U.S. Appl. No. 14/363,890.
Response filed Jun. 23, 2015 to Restriction Requirement dated Apr. 23, 2015 for U.S. Appl. No. 14/363,890.

Final Office Action dated Jun. 25, 2015 for U.S. Appl. No. 11/097,947.
Office Action dated Nov. 10, 2009 for U.S. Appl. No. 11/097,947.
Response filed Mar. 10, 2010 to Office Action dated Nov. 10, 2009 for U.S. Appl. No. 11/097,947.
Final Office Action dated Jun. 7, 2010 for U.S. Appl. No. 11/097,947.
Response filed Oct. 7, 2010 to Final Office Action dated Jun. 7, 2010 for U.S. Appl. No. 11/097,947.
Supplemental response filed May 30, 2013 to Final Office Action dated Jun. 7, 2010 for U.S. Appl. No. 11/097,947.
Office Action dated Jul. 2, 2014 for U.S. Appl. No. 11/097,947.
Response filed Dec. 2, 2014 to Office Action dated Jul. 2, 2014 for U.S. Appl. No. 11/097,947.
U.S. Appl. No. 12/333,465 Non-final Office Action dated Apr. 4, 2014.
U.S. Appl. No. 13/782,203 final Office Action dated Apr. 16, 2014.
U.S. Appl. No. 13/486,002 final Office Action dated Apr. 2014.
Philip Smalley, Evolution of critical illness, Institute and Faculty of Actuaries, Dec. 2005.
U.S. Appl. No. 12/477,225 office action dated Nov. 20, 2014.
Final Office Action dated May 6, 2015 for U.S. Appl. No. 11/903,607.
Written Opinion of the International Searching Authority dated Jan. 15, 2014 for PCT/IB2013/055837 filed Jul. 16, 2013.
International Preliminary Report on Patentability dated Jan. 20, 2015 for PCT/IB2013/055837 filed Jul. 16, 2013.
Final Office Action dated Nov. 15, 2017 for U.S. Appl. No. 14/529,812.
International Search Report completed Dec. 23, 2013 for PCT/IB2013/055837 filed Jul. 16, 2013.
Office Action dated Sep. 21, 2017 for U.S. Appl. No. 12/333,465.
Office Action dated Sep. 19, 2017 for U.S. Appl. No. 14/363,890.
Office Action dated Sep. 19, 2017 for U.S. Appl. No. 14/364,004.
Office Action dated Dec. 28, 2015 for U.S. Appl. No. 11/097,947.
Final Office Action dated Jul. 19, 2010 for U.S. Appl. No. 11/074,453.
Response filed Dec. 20, 2010 to Final Office Action dated Jul. 19, 2010 for U.S. Appl. No. 11/074,453.
Response filed Jan. 7, 2016 to Office Action dated Jul. 8, 2015 for U.S. Appl. No. 11/074,453.
International Search Report for PCT/IB12/56783 (WO2013/084113) dated May 9, 2013.
International Search Report for PCT/IB2012/056827 dated Mar. 19, 2013.
International Preliminary Report on Patentability and Written Opinion for PCT/IB2012/056827 dated Jun. 10, 2014 and dated Mar. 19, 2013.
International Search Report for PCT/IB2012/56780 dated May 2, 2013.
International Preliminary Report on Patentability and Written Opinion for PCT/IB2012/56780 dated Jun. 10, 2014 and dated May 2, 2013.
U.S. Appl. No. 11/794,830 final Office Action dated Jun. 24, 2014.
U.S. Appl. No. 12/477,225, Non-final Office Action dated Mar. 25, 2011.
U.S. Appl. No. 12/122,549, Non-final Office Action dated Mar. 30, 2011.
U.S. Appl. No. 12/333,465, Non-final Office Action dated Mar. 30, 2011.
U.S. Appl. No. 11/189,647, Response to Office Action dated Apr. 18, 2011.
U.S. Appl. No. 12/303,395, Non-Final Rejection dated Apr. 29, 2011.
U.S. Appl. No. 12/303,391, Final Office Action dated May 11, 2011.
U.S. Appl. No. 10/344,176, Office Action dated May 16, 2011.
U.S. Appl. No. 11/074,453, Requirement for Election dated May 23, 2011.
U.S. Appl. No. 12/303,388 Response dated Jun. 8, 2011.
U.S. Appl. No. 12/303,395 Final Office Action date Jun. 13, 2011.
U.S. Appl. No. 12/333,465, Response filed Jun. 30, 2011.
U.S. Appl. No. 12/122,549, Response filed Jul. 21, 2011.
U.S. Appl. No. 12/303,388 Final Office Action dated Jul. 5, 2011.
U.S. Appl. No. 11/189,647, Final Office Action dated Jun. 22, 2011.
U.S. Appl. No. 12/477,225, Non Final Office Action dated Jul. 8, 2011.

(56) References Cited

OTHER PUBLICATIONS

U.S. Appl. No. 12/441,447, Non Final Office Action dated Aug. 1, 2011.
U.S. Appl. No. 12/477,179, Non final office action dated Jul. 22, 2011.
U.S. Appl. No. 12/477,208, Non final office action dated Jul. 22, 2011.
U.S. Appl. No. 12/477,189 non final Office Action dated Aug. 5, 2011.
U.S. Appl. No. 12/303,391 RCE response dated Aug. 11, 2011.
U.S. Appl. No. 11/189,647, Response dated Aug. 12, 2011.
U.S. Appl. No. 12/303,388 Response dated Sep. 2, 2011.
U.S. Appl. No. 12/477,213 Non Final Office Action dated Aug. 9, 2011.
U.S. Appl. No. 12/442,549 non Final Office Action dated Sep. 19, 2011.
U.S. Appl. No. 12/477,225 Final Office Action dated Sep. 28, 2011.
U.S. Appl. No. 12/333,465 Final Office Action dated Oct. 4, 2011.
U.S. Appl. No. 12/477,179, Response filed Oct. 24, 2011.
U.S. Appl. No. 12/122,549, Final Office Action dated Oct. 6, 2011.
U.S. Appl. No. 11/074,453, Office Action dated Oct. 11, 2011.
U.S. Appl. No. 12/912,040, Office Action dated Oct. 20, 2011.
U.S. Appl. No. 12/441,447, Response filed Nov. 1, 2011.
U.S. Appl. No. 12/477,189, Response filed Nov. 4, 2011.
U.S. Appl. No. 12/721,619, Preliminary Amendment filed Nov. 3, 2011.
U.S. Appl. No. 11/903,607, Office Action dated Nov. 30, 2011.
U.S. Appl. No. 12/477,189 Final Office Action dated Dec. 5, 2011.
U.S. Appl. No. 12/912,009 Non-final Office Action dated Dec. 19, 2011.
U.S. Appl. No. 11/794,830, Non-Final Rejection dated Dec. 19, 2011.
U.S. Appl. No. 12/122,549, RCE response dated Jan. 6, 2012.
U.S. Appl. No. 11/074,453, Response filed Jan. 11, 2012.
U.S. Appl. No. 12/477,225, RCE Response filed Jan. 25, 2012.
U.S. Appl. No. 12/333,465, RCE Response filed Jan. 26, 2012.
U.S. Appl. No. 12/303,399 Office Action dated Oct. 11, 2011.
U.S. Appl. No. 13/365,430, filed Feb. 3, 2012.
U.S. Appl. No. 13/365,527, filed Feb. 3, 2012.
U.S. Appl. No. 13/365,566, filed Feb. 3, 2012.
U.S. Appl. No. 12/303,399 Final Office Action dated Mar. 14, 2012.
U.S. Appl. No. 12/112,165, Non Final Office Action dated May 17, 2012.
Response to Office Action filed Aug. 1, 2016 for U.S. Appl. No. 13/641,145.
Final office action dated Aug. 9, 2016 for U.S. Appl. No. 13/386,431.
U.S. Appl. No. 10/344,176, Response to Office Action dated Nov. 9, 2009.
U.S. Appl. No. 11/189,647, filed Jul. 26, 2005.
U.S. Appl. No. 11/189,647, Final Rejection dated May 11, 2010.
U.S. Appl. No. 11/189,647, Non-Final Rejection dated Aug. 14, 2009.
U.S. Appl. No. 11/189,647, Response to Office Action dated Feb. 15, 2010.
U.S. Appl. No. 10/819,256, filed Apr. 6, 2004.
U.S. Appl. No. 10/819,256, Final Rejection dated Jan. 6, 2009.
U.S. Appl. No. 10/819,256, Non-Final Rejection dated Mar. 18, 2008.
U.S. Appl. No. 10/819,256, Response to Office Action dated Sep. 18, 2008.
U.S. Appl. No. 11/097,947, filed Apr. 1, 2006.
U.S. Appl. No. 11/097,947, Non-Final Rejection dated Nov. 10, 2009.
U.S. Appl. No. 11/097,947, Final Rejection dated Jun. 7, 2010.
U.S. Appl. No. 11/097,947, Response to Office Action dated Mar. 10, 2010.
U.S. Appl. No. 10/818,574, filed Apr. 6, 2004.
U.S. Appl. No. 10/818,574, Non-Final Rejection dated Feb. 4, 2009.
U.S. Appl. No. 10/818,574, Response to Office Action dated May 4, 2009.
U.S. Appl. No. 11/074,453, filed Mar. 8, 2005.
U.S. Appl. No. 11/074,453, Non-Final Rejection dated Mar. 4, 2009.
U.S. Appl. No. 11/074,453, Requirement for Election dated Mar. 31, 2010.
U.S. Appl. No. 11/074,453, Notice of Non-compliant response dated Nov. 9, 2009.
U.S. Appl. No. 11/074,453, Response to Office Action dated Apr. 29, 2010.
U.S. Appl. No. 11/074,453, Response to Office Action dated Nov. 23, 2009.
U.S. Appl. No. 11/074,453, Response to Office Action dated Jul. 6, 2009.
U.S. Appl. No. 11/794,830, filed Jan. 22, 2008.
U.S. Appl. No. 11/794,830, Final Rejection dated Dec. 7, 2009.
U.S. Appl. No. 11/794,830, Non-Final Rejection dated May 27, 2009.
U.S. Appl. No. 11/794,830, Response to Office Action dated Sep. 28, 2009.
U.S. Appl. No. 11/794,830, Response to Office Action dated Apr. 7, 2010.
U.S. Appl. No. 11/903,607, filed Sep. 24, 2007.
U.S. Appl. No. 11/903,607, Final Rejection dated Jan. 28, 2010.
U.S. Appl. No. 11/903,607, Non-Final Rejection dated May 13, 2009.
U.S. Appl. No. 11/903,607, Response to Office Action dated Aug. 12, 2009.
U.S. Appl. No. 11/903,607, Response to Office Action dated Apr. 28, 2010.
U.S. Appl. No. 12/442,549, filed Mar. 24, 2009.
U.S. Appl. No. 12/477,179, filed Jun. 3, 2009.
U.S. Appl. No. 12/477,208, filed Jun. 3, 2009.
U.S. Appl. No. 12/477,213, filed Jun. 3, 2009.
U.S. Appl. No. 12/477,225, filed Jun. 3, 2009.
U.S. Appl. No. 12/477,189, filed Jun. 3, 2009.
U.S. Appl. No. 12/721,619, filed Mar. 11, 2010.
U.S. Appl. No. 11/715,181, filed Mar. 7, 2007.
U.S. Appl. No. 11/715,181, Non-Final Rejection dated Nov. 3, 2009.
U.S. Appl. No. 11/715,181, Non-Final Rejection dated May 12, 2010.
U.S. Appl. No. 11/715,181, Response to Office Action dated Feb. 3, 2010.
U.S. Appl. No. 12/303,395, Non-Final Rejection dated Jan. 24, 2011.
U.S. Appl. No. 12/912,009, filed Oct. 26, 2010.
U.S. Appl. No. 12/912,040, filed Oct. 26, 2010.
U.S. Appl. No. 12/112,165, Final Rejection dated Feb. 10, 2011.
U.S. Appl. No. 11/715,181, Response to Office Action dated Mar. 11, 2011.
U.S. Appl. No. 12/303,388, Non-Final Office Action dated Mar. 11, 2011.
What is a no Claim Discount? Posted by Brendan "No Nonsense Insurance Blog" Jun. 25, 2009 (Archived under "A guide to insurance") http://blog.nononsense.ie/2009/06/26what-is-a-no-claims-discount, Jan. 12, 2014.
Response filed Oct. 6, 2014 to Office Action dated Apr. 4, 2014 for U.S. Appl. No. 12/333,465.
Office Action dated Jan. 23, 2015 for U.S. Appl. No. 12/333,465.
Response filed Apr. 20, 2015 to Office Action dated Jan. 23, 2015 for U.S. Appl. No. 12/333,465.
Office Action dated Oct. 7, 2014 for U.S. Appl. No. 12/447,179.
Response filed Feb. 9, 2015 to Office Action dated Sep. 9, 2014 for U.S. Appl. No. 13/641,145.
Final Office Action dated May 4, 2015 for U.S. Appl. No. 13/641,145.
Office Action dated Nov. 7, 2014 for U.S. Appl. No. 13/996,058.
Response filed May 7, 2015 to Office Action dated Nov. 7, 2014 for U.S. Appl. No. 13/996,058.
"What is no claims discount?" Posted by "Brendan" on "No Nonsense Insurance Blog" on Jun. 26, 2009 (archived under "A guide to insurance"), http://blog.nononsense.ie/2009/0626/what-is-a-no-claims-discount, accessed Jan. 12, 2014.
"Why do companies offer different auto insurance discounts and what discounts does Progressive offer?" posted by "Allison Ruuska" on @Progressive Blog—Auto Insurance Discount on Feb. 9, 2009;

(56) References Cited

OTHER PUBLICATIONS http://www.progressive.com/understanding_insurance/entries/2009/9/1/auto_insurance_disc/, accessed Jan. 13, 2014.
U.S. Appl. No. 13/641,155, Non-final Office Action dated Mar. 28, 2014.
U.S. Appl. No. 13/641,143, Non-final Office Action dated Mar. 27, 2014.
U.S. Appl. No. 11/794,830, Supplemental response dated May 18, 2012.
U.S. Appl. No. 12/477,213 Supplemental Response filed Jun. 6, 2012.
U.S. Appl. No. 12/912,040, Supplemental response filed Jun. 14, 2012.
U.S. Appl. No. 12/303,395 Response filed May 11, 2012.
U.S. Appl. No. 13/472,571, filed May 16, 201.
U.S. Appl. No. 13/486,002, filed Jun. 1, 2012.
U.S. Appl. No. 12/477,213 Supplemental Response filed Jul. 9, 2012.
U.S. Appl. No. 12/912,009 Response filed Aug. 31, 2012.
U.S. Appl. No. 13/638,608, filed Sep. 30, 2012.
U.S. Appl. No. 13/648,309, filed Oct. 10, 2012.
U.S. Appl. No. 13/641,143, filed Oct. 15, 2012.
U.S. Appl. No. 13/641,145, filed Oct. 15, 2012.
U.S. Appl. No. 13/641,155, filed Oct. 15, 2012.
U.S. Appl. No. 12/477,225, Final Office Action dated Feb. 4, 2013.
U.S. Appl. No. 13/365,430 office action dated Oct. 1, 2012.
U.S. Appl. No. 13/365,430 response filed Feb. 19, 2013.
Final Office Action dated Mar. 11, 2015 for U.S. Appl. No. 12/303,391.
Connel, Medical tourism,: Sea, sun sand and . . . surgery, Dec. 2006, Tourism management, Volumen 27, Issue 6, pp. 1093-11.
Office Action dated Apr. 8, 2015 for U.S. Appl. No. 13/365,566.
Final Office Action dated Jun. 30, 2016 for U.S. Appl. No. 11/097,947.
Response filed Jun. 29, 2016 to Office Action dated Jan. 15, 2016 for U.S. Appl. No. 14/363,890.
Response filed Jul. 5, 2016 to Office Action dated Feb. 4, 2016 for U.S. Appl. No. 13/386,431.
Response filed Jul. 5, 2016 to Office Action dated Feb. 3, 2016 for U.S. Appl. No. 14/364,004.
International Search Report for PCT/IB05/003842 filed Dec. 21, 2005 (WO2006/072822).
Written Opinion for PCT/IB05/003842 filed Dec. 21, 2005 (WO2006/072822).
International Preliminary Report on Patentability for PCT/IB05/003842 filed Dec. 21, 2005 (WO2006/072822).
International Search Report for PCT/IB07/051945 filed May 23, 2007 (WO2007/141695).
Written Opinion for PCT/IB07/051945 filed May 23, 2007 (WO2007/141695).
International Preliminary Report on Patentability for PCT/IB07/051945 filed May 23, 2007 (WO2007/141695).
International Search Report for PCT/IB07/051946 filed May 23, 2007 (WO2007/141696).
Written Opinion for PCT/IB07/051946 filed May 23, 2007 (WO2007/141696).
International Preliminary Report on Patentability for PCT/IB07/051946 filed May 23, 2007 (WO2007/141696).
International Search Report for PCT/IB07/051947 filed May 23, 2007 (WO2007/141697).
Written Opinion for PCT/IB07/051947 filed May 23, 2007 (WO2007/141697).
International Preliminary Report on Patentability for PCT/IB07/051947 filed May 23, 2007 (WO2007/141697).
International Search Report published Apr. 23, 2009 for PCT/IB07/051948 filed May 23, 2007 (WO2007/141698).
Written Opinion published Mar. 13, 2009 PCT/IB07/051948 filed May 23, 2007 (WO2007/141698).
International Preliminary Report on Patentability published Mar. 17, 2009 for PCT/IB07/051948 filed May 23, 2007 (WO2007/141698).
International Search Report for PCT/IB07/053906 filed Sep. 26, 2007 (WO2008/038232).
Written Opinion for PCT/IB07/053906 filed Sep. 26, 2007 (WO2008/038232).
International Preliminary Report on Patentability for PCT/IB07/053906 filed Sep. 26, 2007 (WO2008/038232).
International Search Report for PCT/IB01/01406 filed Aug. 8, 2001 (WO2002/013438).
International Preliminary Report on Patentability for PCT/IB01/01406 filed Aug. 8, 2001 (WO2002/013438).
International Search Report for PCT/IB2007/053760 filed Sep. 18, 2007 (WO2008/035280).
Written Opinion for PCT/IB2007/053760 filed Sep. 18, 2007 (WO2008/035280).
International Preliminary Report on Patentability for PCT/IB2007/053760 filed Sep. 18, 2007 (WO2008/035280).
International Search Report dated Nov. 2, 2011 for PCT/IB11/51627 (WO2011/128873).
Flexible Spending Account, from Wikipedia encyclopedia, pp. 7, retrieved Sep. 28, 2012.
Article, Health Care Spending Accounts, AHIP America's Health Insurance Plans, pp. 12, retrieved Sep. 28, 2012.
Health Reimbursement Account, from Wikipedia encyclopedia, pp. 4, retrieved Sep. 28, 2012.
Health Savings Account, from Wikipedia encyclopedia, pp. 10, retrieved Sep. 28, 2012.
Saleem—Article, Health Spending Accounts, U.S. Bureau of Labor Statistics, pp. 5, retrieved Sep. 28, 2012.
Long-Term Insurance Act, No. 52, Jan. 1, 1998, Administration of Act, 55 pgs.
Government Gazette, Republic of South Africa, Insurance laws Amendment Act 2008, vol. 521, Cape Town, Nov. 5, 2008, No. 31578, 36 pgs.
Regulation Gazette No. 6652, Government Notice, Medical Schemes Act, vol. 412, Oct. 20, 1999, 67 pgs.
Government Gazette, Republic of South Africa, Staatskoerant, Cape Town, vol. 399, Sep. 23, 1998, No. 19277, 49 pgs.
Barron's Dictionary of Fiance, 3rd Edition, 1995, pp. 503, referenced in office action dated Jan. 31, 2013, U.S. Appl. No. 13/318,620.
U.S. Appl. No. 13/318,620, Non-final Office Action dated Jan. 31, 2013.
U.S. Appl. No. 13/486,002, Non-final Office Action dated Jan. 31, 2013.
AFBIC Insurance Products, Jan. 6, 2009, Captured by internet Archive WayBack Machine . Http;//web.archive.org/web/20090106144129/http://www.afbic.com/products/auto.aspx.
U.S. Appl. No. 13/386,431, Final Office Action dated Mar. 28, 2013.
Life Launch Discoverer—Publication "Intelligent Life Insurance" dated Mar. 2012.
U.S. Appl. No. 13/641,145 non-final Office Action dated Sep. 9, 2014.
U.S. Appl. No. 13/782,203, RCE response filed Sep. 16, 2014.
U.S. Appl. No. 09/876,311, filed Jun. 7, 2001.
U.S. Appl. No. 09/876,311, Final Rejection dated Oct. 23, 2006.
U.S. Appl. No. 09/876,311, Final Rejection dated Dec. 16, 2009.
U.S. Appl. No. 09/876,311, Non-Final Rejection dated Jan. 17, 2006.
U.S. Appl. No. 09/876,311, Non-Final Rejection dated Nov. 30, 2007.
U.S. Appl. No. 09/876,311, Non-Final Rejection dated Jul. 9, 2010.
U.S. Appl. No. 09/876,311, Requirement for Restriction dated May 18, 2007.
U.S. Appl. No. 09/876,311, Requirement for Restriction dated Jan. 2, 2009.
U.S. Appl. No. 09/876,311, Requirement for Restriction dated Jan. 16, 2009.
U.S. Appl. No. 09/876,311, Requirement for Restriction dated Aug. 10, 2009.
U.S. Appl. No. 09/876,311, Response to Office Action dated Jul. 19, 2006.
U.S. Appl. No. 09/876,311, Response to Office Action dated Feb. 23, 2007.

(56) References Cited

OTHER PUBLICATIONS

U.S. Appl. No. 09/876,311, Response to Office Action dated Jul. 17, 2007.
U.S. Appl. No. 09/876,311, Response to Office Action dated May 29, 2008.
U.S. Appl. No. 09/876,311, Response to Office Action dated Oct. 15, 2008.

* cited by examiner

METHOD OF DETERMINING THE ATTENDANCE OF AN INDIVIDUAL AT A LOCATION AND A SYSTEM THEREFOR

CROSS REFERENCE TO RELATED APPLICATIONS

This application claims the benefit of U.S. Provisional Patent Application No. 61/740,540, filed Dec. 21, 2012, the entire contents of which are incorporated herein by reference.

FIELD OF THE INVENTION

The invention relates to a system and method for determining a location of an individual, and in particular, determining attendance of individuals during health related activities.

BACKGROUND OF THE INVENTION

There are applications in which it is required to verify the attendance of an individual at a particular geographic location, such as a gym. It one approach, one person can manually record the presence of another person, either by entry onto a paper form, or by entry into a computer system. In another approach, a person can swipe or tag an identification card at an entrance to the geographic location.

SUMMARY OF THE INVENTION

In accordance with an embodiment of the disclosure, a system for determining participation in a health improvement plan includes at least one computer executing software stored on non-transitory media, the software configured for: storing data pertaining to the identification of a member of the health improvement plan; storing data pertaining to the identification of a mobile computing device associated with the member; storing data pertaining to a set of locations each pertaining to a predetermined health improvement facility; receiving information sent from the mobile computing device pertaining to a location of the mobile computing device within a predetermined distance with respect to a location within the set of locations; storing a time at which a location of the mobile computing device is within the predetermined distance, at a plurality of different times; analyzing the stored time to determine a level of participation of the member with the wellness program; and communicating the level of participation to a manager of the wellness program.

In various embodiments thereof, a session is defined by the continuous presence of the mobile computing device at a health improvement facility for a period of time, and the stored plurality of times corresponds to time information received from the mobile computing device during a single session; and/or analyzing the stored time includes determining a length of a session based upon the plurality of different times.

In further embodiments thereof, a session is defined by the continuous presence of the mobile computing device at a health improvement facility for a period of time; and wherein analyzing includes determining a level of participation of the member in a plurality of sessions; and wherein the plurality of stored times corresponds to time information received from the mobile computing device during a single session, and for a plurality of sessions.

In other embodiments thereof, the level of participation is correlated to a set of ranges of participation corresponding to points; the points information is communicated to a computer associated with a health or wellness related insurance policy; the receiving, storing, analyzing, and communication are carried out for a plurality of members of the health improvement plan; the set of stored locations are obtained from a data source external to the at least one computer and/or the mobile computing device executes software stored on non-transitory media, the mobile software configured to notify at least one of the member and the at least one computer, when the mobile device is within a predetermined distance with respect to a location within the set of locations.

In yet further embodiments thereof, the member can designate, using the mobile computing device, when location information can be sent; the mobile computing device obtains location information using at least one of a triangulation with a cellular network, location data services using the internet, GPS information from satellites; a location of a member is periodically audited to ensure the member is at a location of the mobile computing device associated with the member; and/or analyzing includes comparing location data received by the mobile computing device and the stored plurality of times to determine if the mobile computing device was likely at the same location throughout the session.

In still further embodiments thereof, the user signals to the mobile computing device when the user is leaving a predetermined health improvement facility, and the mobile computing device communicates the signal to the at least one computer; the mobile computing device sends location information to the at least one computer when the user signals to the mobile computing device; and/or the software is further configured to determine an aware based upon the determined level of participation.

In another embodiment of the disclosure, a method for determining participation in a health improvement plan includes using at least one computer executing software stored on non-transitory media, the software configured for: storing data pertaining to the identification of a member of the health improvement plan; storing data pertaining to the identification of a mobile computing device associated with the member; storing data pertaining to a set of locations each pertaining to a predetermined health improvement facility; receiving information sent from the mobile computing device pertaining to a location of the mobile computing device within a predetermined distance with respect to a location within the set of locations; storing a time at which a location of the mobile computing device is within the predetermined distance, at a plurality of different times; analyzing the stored time to determine a level of participation of the member with the wellness program; and communicating the level of participation to a manager of the wellness program.

In a further embodiment of the disclosure, a method for determining participation in a health improvement plan includes using at least one computer executing software stored on non-transitory media, the software configured for: storing data pertaining to the identification of members of the health improvement plan associated with an insurance policy; storing data pertaining to the identification of mobile computing devices associated with the members; storing data pertaining to a set of locations each pertaining to a predetermined health improvement facility; receiving information sent from mobile computing devices pertaining to locations of individual mobile computing devices within a predetermined distance with respect to a location within the set of locations; storing a time at which a location of the individual mobile computing devices are within the predetermined distance, at a plurality of different times; analyzing the stored time to determine lengths of sessions and a number of sessions, a session defined by the continuous presence of the mobile computing device at a predetermined health improvement facility during a period of time; determining a level of participation of individual members using the analyzed stored times and the association of mobile computing devices and members; and communicating the level of participation to a manager of the wellness program, and to a server associated with the insurance policy.

In variations thereof, the member can designate, using the mobile computing device, when location information can be sent; and/or analyzing includes comparing location data received by the individual mobile computing devices and the stored plurality of times to determine if the individual mobile computing devices were likely at the same respective location throughout the session.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
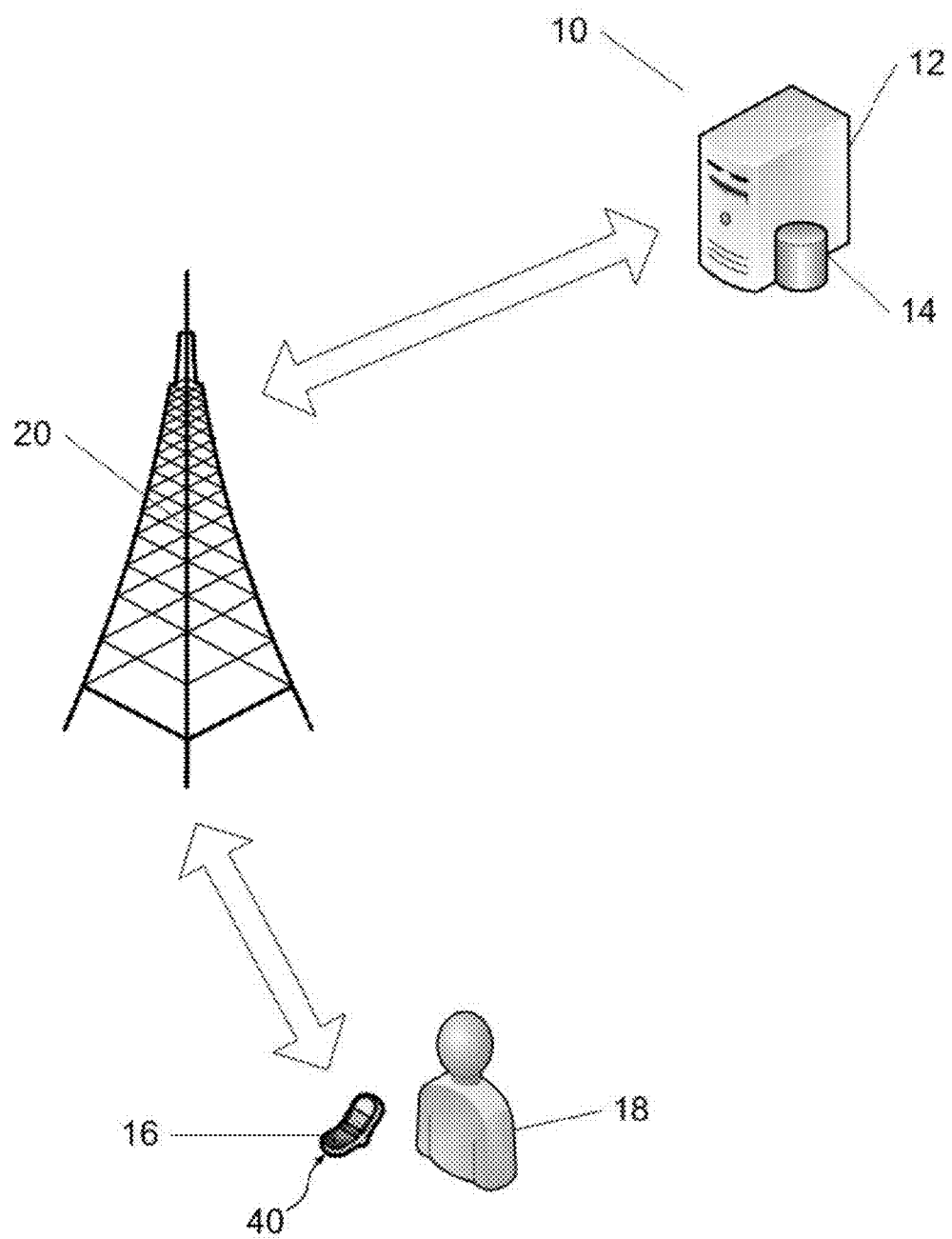
FIG. 1 illustrates an example communication environment of a system of the disclosure.
Figure 2:
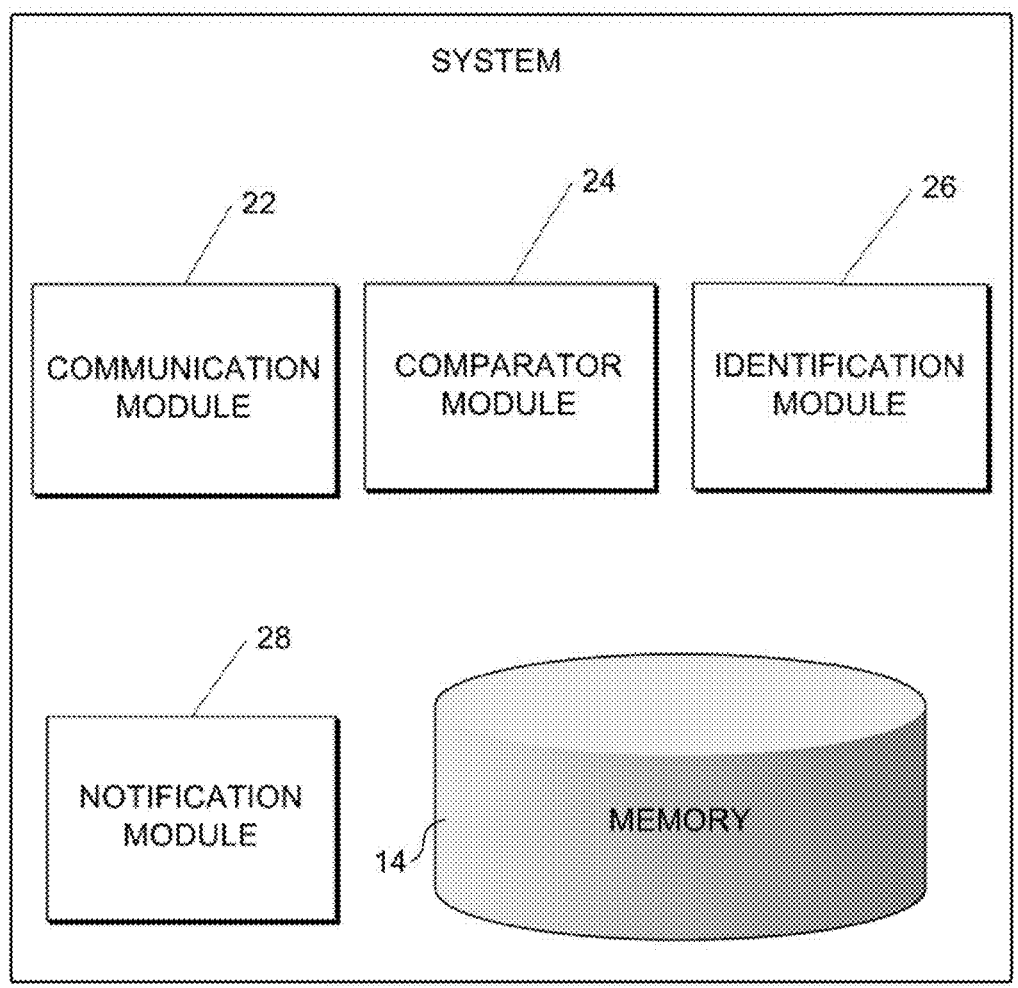
FIG. 2 is a diagrammatic illustration of a system in accordance with the disclosure.
Figure 3:
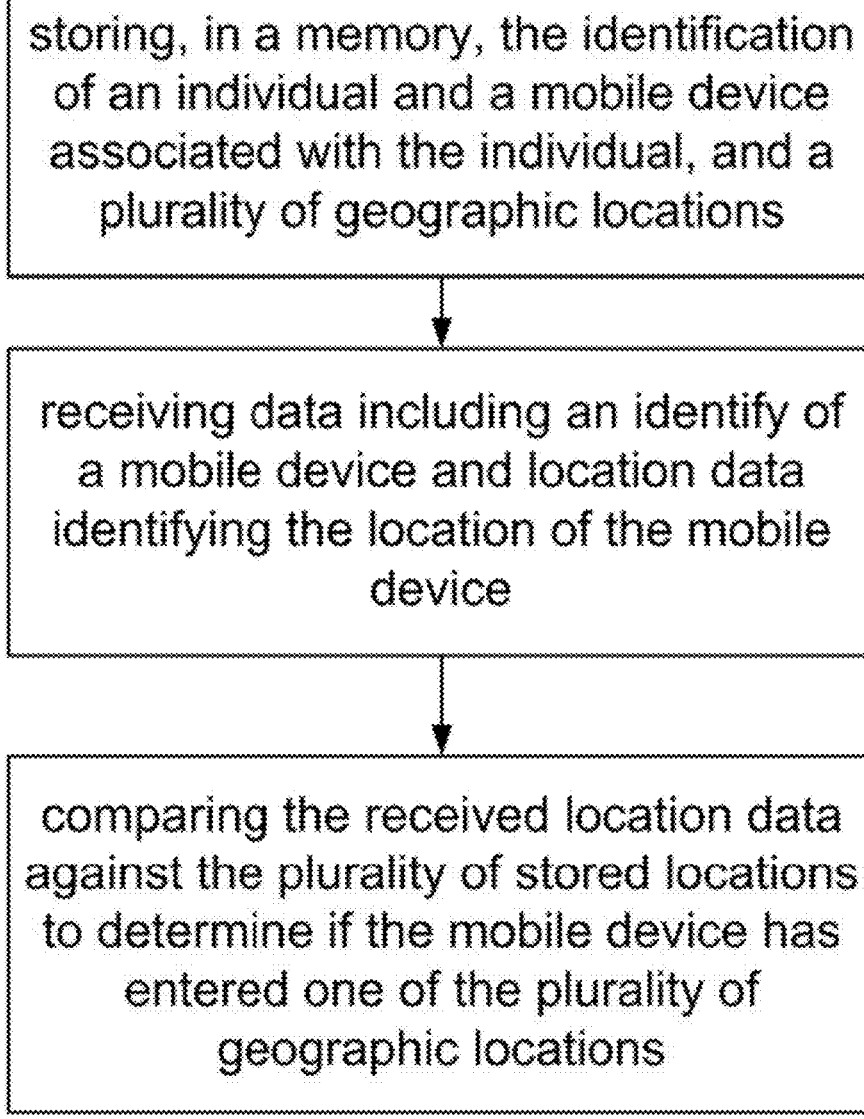
FIG. 3 is a flow chart illustrating a method of the disclosure.

As required, detailed embodiments are disclosed herein; however, it is to be understood that the disclosed embodiments are merely examples and that the systems and methods described below can be embodied in various forms. Therefore, specific structural and functional details disclosed herein are not to be interpreted as limiting, but merely as a basis for the claims and as a representative basis for teaching one skilled in the art to variously employ the present subject matter in virtually any appropriately detailed structure and function. Further, the terms and phrases used herein are not intended to be limiting, but rather, to provide an understandable description of the concepts.

The terms "a" or "an", as used herein, are defined as one or more than one. The term plurality, as used herein, is defined as two or more than two. The term another, as used herein, is defined as at least a second or more. The terms "including" and "having," as used herein, are defined as comprising (i.e., open language). The term "coupled," as used herein, is defined as "connected," although not necessarily directly, and not necessarily mechanically.

The system and methodology described herein relate to a method of determining the attendance of an individual at a location, and a system therefor. The inventors have found that manually recording a person presence is time consuming and requires costly labor. Similarly, swiping or tagging an electronically readable token, such as a card, is expensive and requires additional steps to be taken by the individual and staff at the location. The latter method additionally requires expensive and dedicated hardware and software systems, and possibly communication equipment if the information is to be transmitted elsewhere. The disclosure provides a system and method to reduce the labor and costs associated with determining participation of individuals in health related or other activities, while increasing the quality of the determination.

Referring to the accompanying figures, an information processing system 10 may include a server 12 that includes a number of software modules or subroutines executable on computing hardware, the modules configured to implement the present disclosure, and which are communicative with associated data storage or memory, hereinafter simply referred to as memory 14. In one example embodiment, the modules are implemented by a machine-readable medium embodying instructions which, when executed by a machine, cause the machine to perform any of the methods described above. In another example embodiment, the modules may be implemented using firmware programmed specifically to execute the method described herein.

It will be appreciated that embodiments of the present invention are not limited to such architecture, and could equally well find application in a distributed, or peer-to-peer, architecture system. Thus the modules illustrated could be located on one or more servers or computers, such as system 1000 illustrated in FIG. 5, operated by one or more physically combined or separated institutions. It will also be appreciated that in any of these cases the modules form a physical apparatus with physical modules specifically for executing the steps of the method described herein.

In the illustrated example embodiment, memory 14 is used for storing, at least, the identification of an individual 18 and a mobile device 16 associated with the individual 18, and a plurality of geographic locations, all as described in more detail herein.

A communication module 22 receives data via a communications network 20 from a mobile communications device 16. In the illustrated embodiment the communications network is a mobile communications network. The data received includes identification data including an identity of the mobile communications device 16, and location data identifying the location of the mobile device.

A comparator module 24 compares the received location data against the stored locations and any publicly available or licensed geolocation databases, to determine if the mobile device 16 has entered any particular one of a plurality of predetermined geographic locations. An identification module 26 accesses the memory 14 and uses the identification of the mobile communications device to extract the identity of the user. Thus, software of the disclosure can determined that the individual 18 is located at a particular geographical location.

A notification module 28 issues a notification, in response to the comparator module 24 determining that the mobile device is in one of the plurality of geographic locations. In one example, the location of the mobile device 16 is periodically checked to determine when the device had entered and exited the geographic location.

In another example embodiment, the identification data and location data are transmitted from the mobile communications device 16 on initiation by the user 18. In this example embodiment, an executable application 40 is executed on the mobile device which prompts the user to enter a command via a user interface to send the identification data and location data. The user interface could be one of the existing keys on a keypad of the mobile communications device 16, or alternatively, an object on a touch screen.

Upon exiting the geographic location, the user can again use the user interface to send a data message to the server 12 that they are leaving the location. Alternatively or in addition, a predetermined time after the user enters the geographic location, the location of their mobile device can be automatically checked to ensure that they are still in the geographic location. This data message may once again contain identification data and may or may not include location data.

Figure 4:
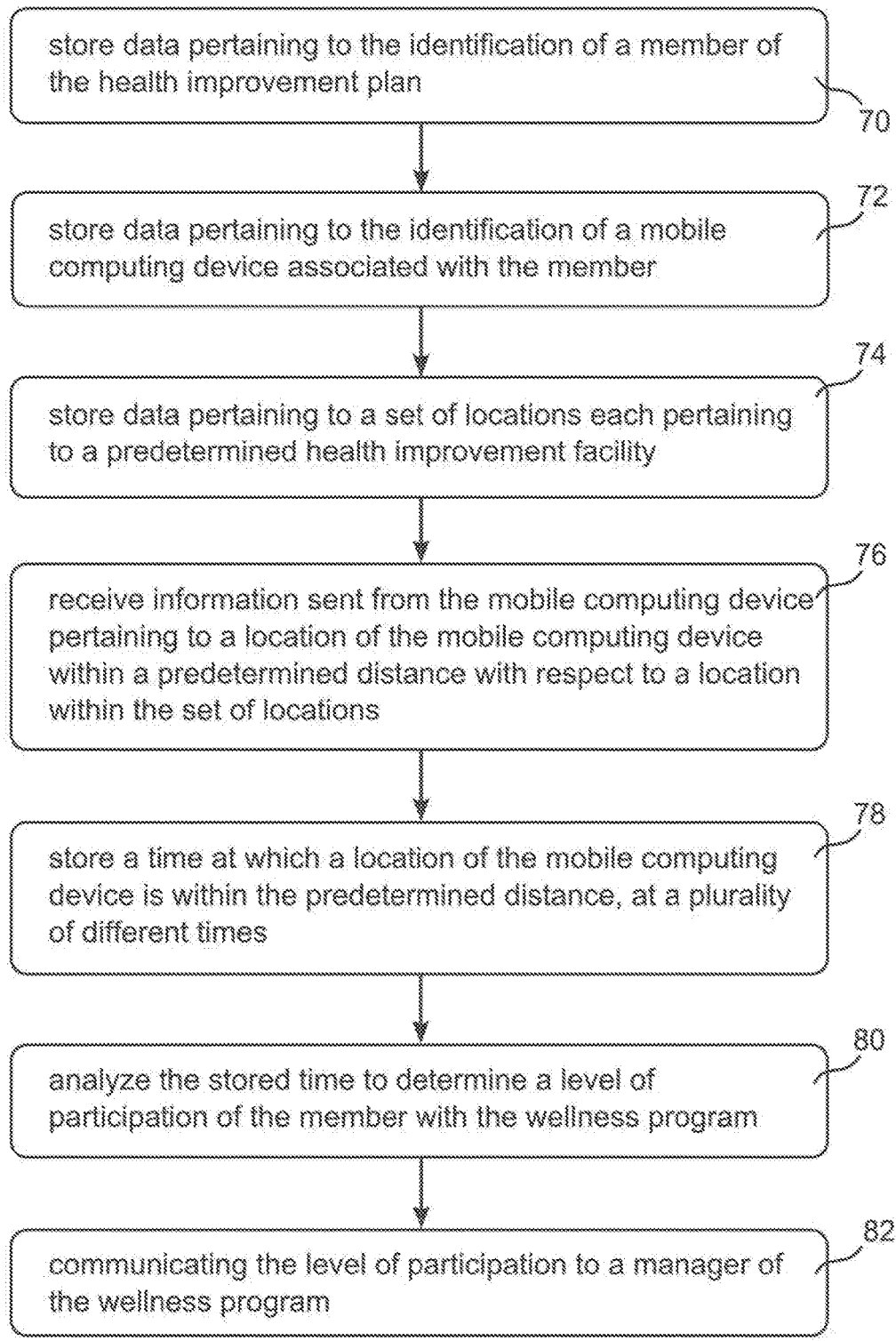
FIG. 4 is a flow chart illustrating an alternative method of the disclosure.

The foregoing process is detailed in FIG. 4, in which includes storing data pertaining to the identification of a member of the health improvement plan (70), storing data pertaining to the identification of a mobile computing device associated with the member (72), storing data pertaining to a set of locations each pertaining to a predetermined health improvement facility (74), receiving information sent from the mobile computing device pertaining to a location of the mobile computing device within a predetermined distance with respect to a location within the set of locations (76), storing a time at which a location of the mobile computing device is within the predetermined distance, at a plurality of different times (78), analyzing the stored time to determine a level of participation of the member with the wellness program (80), and communicating the level of participation to a manager of the wellness program (82).

A system of the disclosure can further be implemented to determine the attendance of an individual at a particular location, as follows. The individual user 18 downloads executable application 40 onto a mobile communication device 16 associated with user 18, via network 20. Application 40 may be written to run natively on both iOS 4.0+ and ANDROID 2.2+ mobile devices, for example. For an iPHONE, it can be written using the OBJECTIVE C programming language, and for ANDROID, it can be written using the JAVA programming language, for example the DALVIK JVM. Alternatively, application 40 can be executed as a web browser page. Further, other programming approaches may be used for the foregoing devices, or any other device of suitable capabilities which user 18 can physically transport as user 18 moves from place to place.

Unless user 18 has previously agreed to be monitored by hardware and software of the disclosure at all times, or when the user is in specific geographic areas or during certain periods of time, the user can select when to run application 40 on their mobile communication device 16.

The user registers or otherwise identifies themselves to server 12, and can communicate with the communication module 22 either by using the mobile communication device 16, or any other electronic device to access the server 12 via the mobile communications network 20, or another communications network, as appropriate. The identification can include the user's name or identification data, and can include IMEI (International Mobile Equipment Identity Number) data, or SIM (Subscriber Identity Module) data.

The user enters the identifying information, as well as an identification of the mobile communication device. The user can also select a personal identification number. The user identification and mobile communication device identification are stored in memory 14 for later use. In addition to the foregoing, the managers of the system 10 will have stored in memory 14 a plurality of geographic locations. The geographic coordinates can be obtained from stored location data or from any publicly available or licensed geolocation service, for example GOOGLE, or via any other known or hereinafter developed method. For example, the GPS coordinates of the geographic locations can be stored in memory 14. The plurality of locations correspond to particular locations at which it is desired to monitor the individual, for example to monitor the use by user 18 of health related facilities. The location can alternatively correspond to an exercise route, and a speed at which the route is undertaken can be obtained from location data.

In one example embodiment, a gym location database stored on a computer server can be updated on a regular basis, for example weekly, and the locations can be geocoded (for example using latitude and longitude codes. The geocoding can be performed before, after, or during the database load process, for example using the GOOGLE MAPS API.

Figure 6:
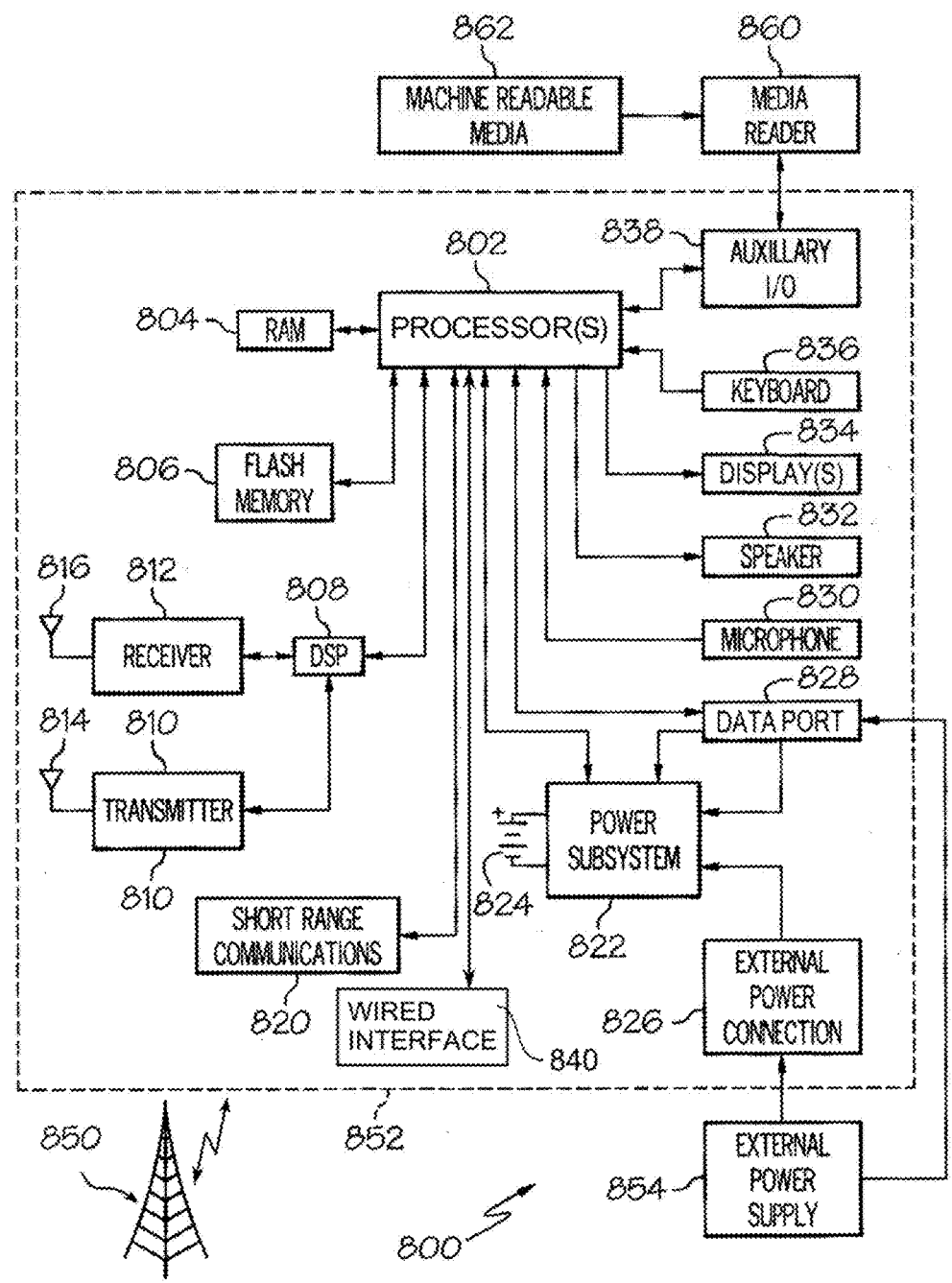
FIG. 6 is an exemplary mobile computing system which can be used in carrying out the disclosure.

When user 18 arrives at a geographic location of interest, and wishes to signal or inform the system that they are present at the location, they can use application 40 of the disclosure which is executing upon the mobile communications device 16 associated with user 18. For example, if the mobile communications device 16 has a touchscreen, the application 40 may display one or more buttons or touch zones on the touchscreen, with appropriate wording such as 'check in' or 'check out'. The check in data can be sent upon pressing the 'check in' button or zone, or alternatively, another button or zone on the touchscreen can be pressed to confirm or to carry out mobile communication which will transmit data corresponding to a location of user 18 and the one or more buttons or zones pressed, using the communications network 20, which transfers information via communications module 22. An example device for carrying out communications from a mobile device is illustrated in FIG. 6.

The data transmitted will include an identity of the mobile communications device 16 which could also be in any one of a number of formats. In one embodiment, the identity used is a username and password entered by the user at the time of entering the health related facility. Alternatively or in addition to the foregoing, the identity can be the SIM or IMEI number of the mobile computing device, or a MAC address associated with the device, or a serial number associated with software of the disclosure executing upon the device.

In addition, the GPS coordinates of the mobile communications device 16 can be transmitted to a server of the disclosure, in one embodiment, to provide location data. The GPS coordinates are obtained by the application 40 which, on receipt of the enter or exit command, calculates these GPS coordinates using the global satellite network and or Wi-Fi location services, or any other geolocating service known or hereinafter developed.

The comparator module 24 compares the received location coordinates, for example GPS coordinates, with the stored location coordinates corresponding to stored locations, and thereby determines if the mobile communication device 16 is at one of the plurality of predetermined geographic locations. An identification module 26 accesses memory 14 to identify the particular user 18 identified, against user information stored in memory 14, as the user of the mobile communications device 16. Once provided with location and user data, a system 10 of the disclosure can determine that a particular user 18 is at a particular geographic location. It is understood that user 18 can leave the mobile computing device 16 at the geographic location and depart, and this must be considered against the importance of accurate location information for the individual. Suitable measures, for example random auditing, can be employed to address such a possibility. When the user is prepared to leave the location, they can signal their departure using device 16, or device 16 can automatically indicate the departure, if authorized. Software of the disclosure executing on mobile communication device 16 then transmits an exit data message to server 12, indicating that the user is now leaving the geographic location.

In an embodiment, software of the disclosure executing upon device 16 compares a location of user 18 at all times, but transmits no location information unless user 18 is located at one of a plurality of predetermined locations whose coordinates are stored within or accessible to device 16. In this manner, device 16 is programmed to transmit location information, but only when at one of such predetermined locations, and privacy of user 18 is optimized. The stored locations may or may not be auditable by user 18.

In one example embodiment, device 16 transmits coordinates when user 18 has arrived at a predetermined location. Alternatively or in addition, device 16 is poled by server 12 at predetermined intervals, for example every 30 minutes, to determine if a user has arrived at, or is still located at, a geographic location. In a yet further alternative, device 16 sends location information to server 12 at intervals.

In one example embodiment, when device 16 transmits location information, the current GPS coordinates of device 16 are transmitted to server 12. In other example embodiment, an address location, or a code corresponding to a location, is transmitted.

In a further example embodiment, each data message transmitted from the mobile communication device 16 includes a timestamp, so that comparator module 24 of server 12 can determine what time the user 18 entered the geographic location and exited the geographic location. In this embodiment, the user will be required to enter the exit button or otherwise signal an exit, before they leave the geographic location, so that their continued presence at the location can be verified using the GPS coordinates of the mobile communication device 16.

One application of the system and method of the disclosure is in the context of a health improvement or wellness program. A wellness program is a set of physical activities, educational activities, and/or other therapeutic activities, which promote the member's physical or mental health. In this example, a member's engagement with the wellness program needs to be monitored to ascertain if the member is in fact engaged in predetermined activities associated with the wellness program. Various components of the wellness program may require the member's physical presence at a predetermined geographic location. In the case of a wellness program, for example, the geographic locations may be health related facilities. For example, the member may need to attend a gym for a predetermined number of times within a period, for example within a month or year.

In accordance with the disclosure, an event is discrete session of activity, for example a workout session, or a therapy session, requiring the attendance of a participant throughout the event. Accordingly, a system of the disclosure determines if the time and location parameters of a session are consistent with having attending and participated in the session. The system further tracks participation at sessions over a number of sessions, to determine compliance with an agreed protocol of sessions for a participant/user, the protocol deemed by health experts to be likely beneficial to the health of the participant if adhered to.

The geographic locations of the gyms are stored in memory 14. When user 18 arrives at the gym, they can signal to the mobile communications device 16, using buttons or other interface, that they are physically present at the gym. The device can then confirm this physical location in transmission to server 12. When user 18 leaves the gym, they can press an 'exit' button, or otherwise signal device 16 and server 10, to register that they are leaving the predetermined location. At this point, server 10 can evaluate whether user 18 has been present at the predetermined location for the required duration. It will be appreciated that in this example, the time of entry and the time of exit are important to ensure that user 18 is at the gym for a minimum amount of time in order to meet commitments under the wellness plan.

In one example implementation, a RESTful JSON web services API is developed under Java that will enable device 16 to securely query server 12 over HTTPS for supported locations within a gym network that are within an allowable proximity of device 16. Application 40 attains the user's geolocation coordinates by using a combination of the device GPS (as applicable) and network/location services, or in any other known or hereinafter developed method. For example, application 40 can call the GOOGLE MAPS API via web services to plot the nearby locations on the map, using a combination of the TVG location database, FOURSQUARE's location services and the member's geolocation. It should be appreciated that in instances where the stored geographic locations are stored in a remote memory, such as when using Foursquare's location services, the system can access the remote memory by way of communications module 22, or in any other known manner.

Once the user has selected the gym and started their workout session, the mobile device can periodically re-acquire the user's geolocation coordinates, and compare them against the coordinates of the gym location to determine if the member's proximity is within the allowable thresholds of proximity. If device 16 is not able to acquire the member's geolocation, due to network connectivity issues, for example, for a predefined number of attempts, or it acquires a location that is outside of the allowable proximity thresholds, confirmation of the workout session at the location may not be successful. If device 16 is able to successfully acquire the member's geolocation within the allowable proximity thresholds, and upon a predetermined number of occasions within a predetermined time period, it can designate the workout session as 'achieved' and send a corresponding event message to server 12, for example to the TVG system, via the secure web services API. The event message can correspond to credits or points or fractional points under the wellness plan. In an embodiment the credits or points are communicated to one or more servers associated with an insurance policy, the data used to determine, for example, premium levels, benefit levels, awards status, coverage limits, inclusions, exclusions, and/or other aspects of insurance coverage. The type of insurance can include health, disability, life, or any other type of insurance where the health of the insured member is relevant.

In this example embodiment, communication module 22 periodically receives data including an identity of the mobile device and location data identifying the location of mobile device 16. Comparator module 24, in response to receiving the data, compares the received location data against the previously received location data corresponding to predetermined wellness locations, to determine if mobile device 16 is in the correct geographic location, or the same geographic location as was previously determined. Comparator module 24 can store an entry time in memory 14 corresponding to at least the first time at which it was determined that mobile communications device 16 entered the geographic location. This information can be used later in a process of the disclosure, to determine an elapsed time at the predetermined location, using the time of exit data received by module 24 corresponding to an indication that device 16 has exited, or is intending to exit the geographic location.

More particularly, exit data can include an identity of mobile device 16, and location data identifying the location of the mobile device at the time the exit data is received. Comparator module 24, in response to receiving the exit data, compares the received location data against the previously received location data to determine if the mobile device is in the same geographic location as was previously determined. Comparator module 24 uses the time of receipt of the exit data and the previously mentioned entry time to determine the amount of time the mobile communications device has been at the geographic location. In one embodiment, an awards module (not shown) associated with server 10 or another server, makes an award to the user 18 under a wellness incentive plan, based at least partially on this length of time at the predetermined health benefiting location.

In an embodiment, a GPS API associated with device 16 has a built-in capability to determine accuracy. In order to authenticate arrival at a predetermined location, for example to indicate the start of a physical activity or workout, it can be required that a reasonable degree of accuracy can achieved and/or confirmed, for example that user 18 is within 50 feet of the predetermined location. For example, an unhealthy location may be located close in proximity to a health improvement facility, particularly in an urban area.

Multiple gyms or other wellness facilities could be located in the same building, or very close to each other, for example on nearby floors. Accordingly, an ability to select from a list of proximate predetermined facilities, displayed by device 16, can be provided.

In some cases, it may not be possible to acquire a GPS signal inside of a building. Accordingly, inside the gym, a wireless/wired LAN or WAN network-based location service can be used to provide at least a minimum level of location accuracy. Therefore, system 10 can calculate whether user 18 is within a range of possible coordinates given the available accuracy, and can either validate that the gym or other predetermined is located within that range, or can provisionally validate the location, and attempt to obtain more accurate location data by GPS or cell triangulation when the user moves device 16 into a suitable range. An exemplary message format between server 12 and device 16, in this example a specification for a "Nearby Gym Locations Get" service, is outlined in Table 1.

TABLE 1

Nearby Gym Locations Get Message Format

| Name | Description | Type | Required | Default | Value |
|---|---|---|---|---|---|
| latitude | Current Mobile Latitude Coordinate | String | Yes | | |
| longitude | Current Mobile Longitude Coordinate | String | Yes | | |
| Proximity | Specifies proximity of gyms to return | String | Yes | | |

Response
Example positive response:
{
  "status": 1,
  "data": {
    "nearby_gyms": [

TABLE 1-continued

Nearby Gym Locations Get Message Format

```
{
    "gym_identifier": "IL332",
    "gym_proximity": "250ft",
    "display_name": "LA FITNESS",
    "gym_address": "123 weight loss rd, Chicago, il 60611",
    "gym_phone": "555-333-2222"
      "gym_lat":"40.234242"
      "gym_long":"90.12313"
   },
   {
    "gym_identifier": "IL412",
    "gym_proximity": "300ft",
    "display_name": "BALLY'S FITNESS",
    "gym_address": "321 weight loss rd, Chicago, il 60611",
    "gym_phone": "555-555-5555"
      "gym_lat":"41.234242"
      "gym_long":"91.12313"
   }
 ]
}
}
```
Example negative response:
{
  "status": 0,
  "errors": [
    {
      "101": "nearby_gym_locations_nonefound."
    }
  ]
}

In accordance with the disclosure, predetermined geographic locations can correspond, for example, to a locations of a SMOKE ENDERS course, a WEIGHT WATCHERS meeting, a group therapy location, a gym or exercise course, or a medical practitioners office.

The disclosure enables users to check-in at health related location without the need for infrastructure to be provided at the locations. Further, users 18 can easily demonstrate their attendance at a location, with little or no interaction required by user 18. Further, there is no need for direct integration, or even cooperative association, between a wellness entity and the wellness plan with which a user 18 is a member, in order to determine participation by members in the wellness plan, and to allocate rewards under the wellness plan.

Example Computer System

Figure 5:
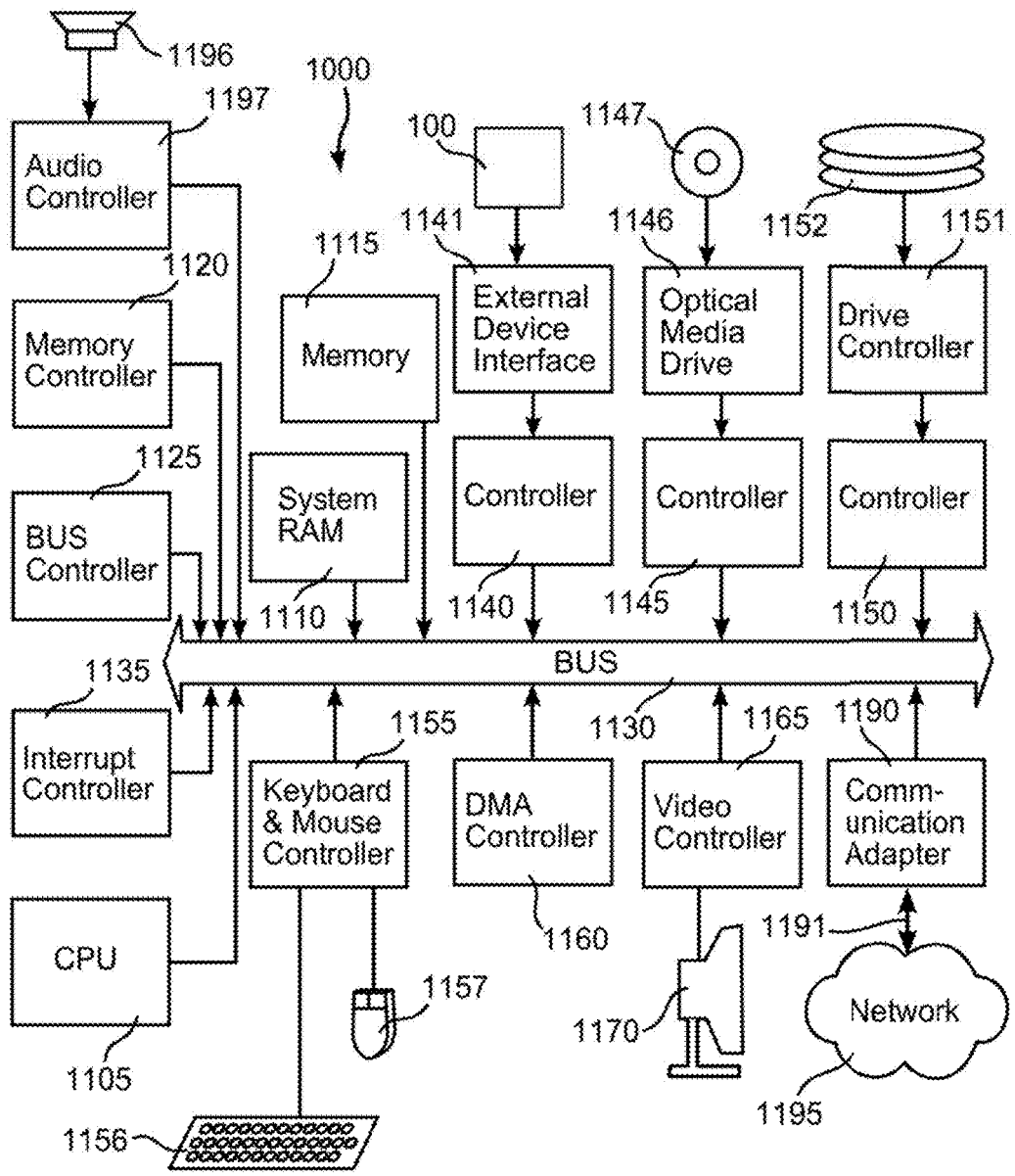
FIG. 5 is an example computer system which can be used in carrying out the disclosure.

FIG. 5 illustrates the system architecture for a computer system 1000, such as a process controller, or other processor on which or with which the disclosure may be implemented. The example computer system of FIG. 5 is for descriptive purposes only. Although the description may refer to terms commonly used in describing particular computer systems, the description and concepts equally apply to other systems, including systems having architectures dissimilar to FIG. 10.

Computer system 1000 includes at least one central processing unit (CPU) 1105, or server, which may be implemented with a conventional microprocessor, a random access memory (RAM) 1110 for temporary storage of information, and a read only memory (ROM) 1115 for permanent storage of information. A memory controller 1120 is provided for controlling RAM 1110.

A bus 1130 interconnects the components of computer system 1000. A bus controller 1125 is provided for controlling bus 1130. An interrupt controller 1135 is used for receiving and processing various interrupt signals from the system components.

Mass storage may be provided by DVD ROM 1147, or flash or rotating hard disk drive 1152, for example. Data and software, including software 400 of the disclosure, may be exchanged with computer system 1000 via removable media such as diskette, CD ROM, DVD, Blu Ray, or other optical media 1147 connectable to an Optical Media Drive 1146 and Controller 1145. Alternatively, other media, including for example a media stick, for example a solid state USB drive, may be connected to an External Device Interface 1141, and Controller 1140. Additionally, a device 100 in accordance with the disclosure may be connected to computer system 1000 through External Device Interface 1141, for example by a USB connector, BLUETOOTH connector, Infrared, or WiFi connector, although other modes of connection are known or may be hereinafter developed. A hard disk 1152 is part of a fixed disk drive 1151 which is connected to bus 1130 by controller 1150. It should be understood that other storage, peripheral, and computer processing means may be developed in the future, which may advantageously be used with the disclosure.

User input to computer system 1000 may be provided by a number of devices. For example, a keyboard 1156 and mouse 1157 are connected to bus 1130 by controller 1155. An audio transducer 1196, which may act as both a microphone and a speaker, is connected to bus 1130 by audio controller 1197, as illustrated. It will be obvious to those reasonably skilled in the art that other input devices, such as a pen and/or tablet, Personal Digital Assistant (PDA), mobile/cellular phone and other devices, may be connected to bus 1130 and an appropriate controller and software, as required. DMA controller 1160 is provided for performing direct memory access to RAM 1110. A visual display is generated by video controller 1165 which controls video display 1170. Computer system 1000 also includes a communications adapter 1190 which allows the system to be interconnected to a local area network (LAN) or a wide area network (WAN), schematically illustrated by bus 1191 and network 1195.

Operation of computer system 1000 is generally controlled and coordinated by operating system software, such as a Windows system, commercially available from Microsoft Corp., Redmond, Wash. The operating system controls allocation of system resources and performs tasks such as processing scheduling, memory management, networking, and I/O services, among other things. In particular, an operating system resident in system memory and running on CPU 1105 coordinates the operation of the other elements of computer system 1000. The present disclosure may be implemented with any number of commercially available operating systems.

One or more applications, such as an HTML page server, or a commercially available communication application, may execute under the control of the operating system, operable to convey information to a user.

Example Mobile Computing Device

FIG. 6 is a block diagram of an electronic device and associated components 800, which can be used in carrying out the disclosure. In this example, an electronic device 852 is a wireless two-way communication device with voice and data communication capabilities. Such electronic devices communicate with a wireless voice or data network 850 using a suitable wireless communications protocol. Wireless voice communications are performed using either an analog or digital wireless communication channel. Data communications allow the electronic device 852 to communicate with other computer systems via the Internet. Examples of electronic devices that are able to incorporate the above described systems and methods include, for example, a data messaging device, a two-way pager, a cellular telephone with data messaging capabilities, a wireless Internet appliance or a data communication device that may or may not include telephony capabilities.

The illustrated electronic device 852 is an example electronic device that includes two-way wireless communications functions. Such electronic devices incorporate communication subsystem elements such as a wireless transmitter 810, a wireless receiver 812, and associated components such as one or more antenna elements 814 and 816. A digital signal processor (DSP) 808 performs processing to extract data from received wireless signals and to generate signals to be transmitted. The particular design of the communication subsystem is dependent upon the communication network and associated wireless communications protocols with which the device is intended to operate.

The electronic device 852 includes a microprocessor 802 that controls the overall operation of the electronic device 852. The microprocessor 802 interacts with the above described communications subsystem elements and also interacts with other device subsystems such as flash memory 806, random access memory (RAM) 804, auxiliary input/output (I/O) device 838, data port 828, display 834, keyboard 836, speaker 832, microphone 830, a short-range communications subsystem 820, a power subsystem 822, and any other device subsystems.

A battery 824 is connected to a power subsystem 822 to provide power to the circuits of the electronic device 852. The power subsystem 822 includes power distribution circuitry for providing power to the electronic device 852 and also contains battery charging circuitry to manage recharging the battery 824. The power subsystem 822 includes a battery monitoring circuit that is operable to provide a status of one or more battery status indicators, such as remaining capacity, temperature, voltage, electrical current consumption, and the like, to various components of the electronic device 852.

The data port 828 of one example is a receptacle connector 104 or a connector that to which an electrical and optical data communications circuit connector 800 engages and mates, as described above. The data port 828 is able to support data communications between the electronic device 852 and other devices through various modes of data communications, such as high speed data transfers over an optical communications circuits or over electrical data communications circuits such as a USB connection incorporated into the data port 828 of some examples. Data port 828 is able to support communications with, for example, an external computer or other device.

Data communication through data port 828 enables a user to set preferences through the external device or through a software application and extends the capabilities of the device by enabling information or software exchange through direct connections between the electronic device 852 and external data sources rather then via a wireless data communication network. In addition to data communication, the data port 828 provides power to the power subsystem 822 to charge the battery 824 or to supply power to the electronic circuits, such as microprocessor 802, of the electronic device 852.

Operating system software used by the microprocessor 802 is stored in flash memory 806. Further examples are able to use a battery backed-up RAM or other non-volatile storage data elements to store operating systems, other executable programs, or both. The operating system software, device application software, or parts thereof, are able to be temporarily loaded into volatile data storage such as RAM 804. Data received via wireless communication signals or through wired communications are also able to be stored to RAM 804.

The microprocessor 802, in addition to its operating system functions, is able to execute software applications on the electronic device 852. A predetermined set of applications that control basic device operations, including at least data and voice communication applications, is able to be installed on the electronic device 852 during manufacture. Examples of applications that are able to be loaded onto the device may be a personal information manager (PIM) application having the ability to organize and manage data items relating to the device user, such as, but not limited to, e-mail, calendar events, voice mails, appointments, and task items.

Further applications may also be loaded onto the electronic device 852 through, for example, the wireless network 850, an auxiliary I/O device 838, Data port 828, short-range communications subsystem 820, or any combination of these interfaces. Such applications are then able to be installed by a user in the RAM 804 or a non-volatile store for execution by the microprocessor 802.

In a data communication mode, a received signal such as a text message or web page download is processed by the communication subsystem, including wireless receiver 812 and wireless transmitter 810, and communicated data is provided the microprocessor 802, which is able to further process the received data for output to the display 834, or alternatively, to an auxiliary I/O device 838 or the Data port 828. A user of the electronic device 852 may also compose data items, such as e-mail messages, using the keyboard 836, which is able to include a complete alphanumeric keyboard or a telephone-type keypad, in conjunction with the display 834 and possibly an auxiliary I/O device 838. Such composed items are then able to be transmitted over a communication network through the communication subsystem.

For voice communications, overall operation of the electronic device 852 is substantially similar, except that received signals are generally provided to a speaker 832 and signals for transmission are generally produced by a microphone 830. Alternative voice or audio I/O subsystems, such as a voice message recording subsystem, may also be implemented on the electronic device 852. Although voice or audio signal output is generally accomplished primarily through the speaker 832, the display 834 may also be used to provide an indication of the identity of a calling party, the duration of a voice call, or other voice call related information, for example.

Depending on conditions or statuses of the electronic device 852, one or more particular functions associated with a subsystem circuit may be disabled, or an entire subsystem circuit may be disabled. For example, if the battery temperature is low, then voice functions may be disabled, but data communications, such as e-mail, may still be enabled over the communication subsystem.

A short-range communications subsystem 820 provides for data communication between the electronic device 852 and different systems or devices, which need not necessarily be similar devices. For example, the short-range communications subsystem 820 includes an infrared device and associated circuits and components or a Radio Frequency based communication module such as one supporting Bluetooth® communications, to provide for communication with similarly-enabled systems and devices, including the data file transfer communications described above.

A media reader 860 is able to be connected to an auxiliary I/O device 838 to allow, for example, loading computer readable program code of a computer program product into the electronic device 852 for storage into flash memory 806. One example of a media reader 860 is an optical drive such as a CD/DVD drive, which may be used to store data to and read data from a computer readable medium or storage product such as computer readable storage media 862. Examples of suitable computer readable storage media include optical storage media such as a CD or DVD, magnetic media, or any other suitable data storage device. Media reader 860 is alternatively able to be connected to the electronic device through the Data port 828 or computer readable program code is alternatively able to be provided to the electronic device 852 through the wireless network 850.

All references cited herein are expressly incorporated by reference in their entirety. It will be appreciated by persons skilled in the art that the present invention is not limited to what has been particularly shown and described herein above. In addition, unless mention was made above to the contrary, it should be noted that all of the accompanying drawings are not to scale. There are many different features to the present invention and it is contemplated that these features may be used together or separately. Thus, the invention should not be limited to any particular combination of features or to a particular application of the invention. Further, it should be understood that variations and modifications within the spirit and scope of the invention might occur to those skilled in the art to which the invention pertains. Accordingly, all expedient modifications readily attainable by one versed in the art from the disclosure set forth herein that are within the scope and spirit of the present invention are to be included as further embodiments of the present invention.

What is claimed is:

1. A system for determining participation in a wellness plan, comprising:
    at least one computer executing software stored on computer readable media, the software configured to enable the server for:
    storing data pertaining to the identification of a member of the wellness plan;
    storing data pertaining to the identification of a cellular phone associated with the member;
    storing data pertaining to a set of locations each pertaining to a predetermined wellness facility associated with the wellness plan;
    receiving information sent from the pertaining to a location of the cellular phone and a duration of time at locations within the set of locations, the cellular phone sending the information to the server without a requirement for action by the member and using geolocation services of the cellular phone;
    storing a plurality of different times at which a location of the cellular phone is within a predetermined distance of a location within the set of locations;
    analyzing the stored plurality of different times to determine a level of participation of the member with the wellness program, wherein the analyzing includes comparing location data received from the cellular phone and the stored plurality of different times to determine one or more participation sessions associated with the location data and to further determine, for each of the one or more participation sessions, if the likelihood that the cellular phone was at the same location throughout the participation session exceeds a threshold: and
    determining an award for the member based upon the determined level of participation in the wellness plan.

2. The system of claim 1, wherein a session is defined by the continuous presence of the cellular phone at a wellness facility for a period of time, and the stored plurality of times corresponds to time information received from the cellular phone during a single session.

3. The system of claim 2, wherein analyzing the stored time includes determining a length of a session based upon the plurality of different times.

4. The system of claim 1, wherein a session is defined by the presence of the cellular phone at a wellness facility for a period of time; and
 wherein analyzing includes determining a level of participation of the member in a plurality of sessions; and
 wherein the plurality of stored times corresponds to time information received from the cellular phone during a single session, and for a plurality of sessions.

5. The system of claim 1, wherein the wellness facility provides a service selected from the group consisting of smoking cessation, weight loss, medical practitioner, and gym.

6. The system of claim 1, wherein the award has the form of points.

7. The system of claim 1, wherein the receiving, storing, analyzing, and communication are carried out for a plurality of members of the wellness plan.

8. The system of claim 1, wherein the set of stored locations are obtained from a data source external to the at least one computer.

9. The system of claim 1, wherein the cellular phone executes software stored on computer readable media, the software configured to notify at least one of the member and the at least one computer, when the cellular phone is within a predetermined distance with respect to a location within the set of locations.

10. The system of claim 1, wherein the award is communicated to a partner of the wellness plan to enable direct integration.

11. The system of claim 1, wherein the geolocation services includes at least one of network location services, a global satellite network, and WiFi locations services.

12. The system of claim 1, wherein the geolocation service provides GPS coordinates.

13. A method for determining participation in a wellness plan, comprising:
 using at least one computer executing software stored on computer readable media, the software configured to enable the computer for:
 storing data pertaining to the identification of a member of the wellness plan;
 storing data pertaining to the identification of a cellular phone associated with the member;
 storing data pertaining to a set of locations each pertaining to a predetermined wellness facility;
 receiving information sent from the cellular phone pertaining to a location of the cellular phone within a predetermined distance with respect to a location within the set of locations, the location information obtained by the cellular phone using geolocation without a requirement for action by the member, the cellular phone only sending the information when the cellular phone has determined that it is within the predetermined distance with respect to a location within the set of locations;
 storing a time at which a location of the cellular phone is within the predetermined distance, at a plurality of different times;
 analyzing the stored time to determine a level of participation of the member with the wellness program, wherein the analyzing includes comparing location data received from the cellular phone and the stored plurality of different times to determine one or more participation sessions associated with the location data and to further determine, for each of the one or more participation sessions, if the likelihood that the cellular phone was at the same location throughout the participation session exceeds a threshold: and
 determining an award for the member based upon the determined level of participation in the wellness plan.

14. A method for determining participation in a health improvement plan, comprising:
 using at least one computer server executing software stored on computer readable media, the software configured to enable the computer for:
 storing data pertaining to the identification of members of the health improvement plan;
 storing data pertaining to the identification of cellular phones each associated with one of the members;
 storing data pertaining to a set of locations each pertaining to a predetermined health improvement facility;
 receiving, from each of the cellular phones, pertaining to locations of the cell phone within a predetermined distance with respect to a location within the set of locations, each of the cellular phones sending the information to the server without a requirement for action by the member associated with the cellular phone and using geolocation services of the cellular phone, each of the cellular phones comparing a current location of the cellular phone with one or more predetermined locations stored within the cellular phone and sending the received information only when the current location and a predetermined location correspond;
 storing, for each of the cellular phones, a plurality of different times at which a location of the cellular phone is within the predetermined distance;
 analyzing, for each of the cellular phones, the stored plurality of different times to determine lengths of sessions and a number of sessions, a session defined by the continuous presence the cellular phone at a predetermined health improvement facility during a period of time;
 determining, for each of the members, a level of participation of the member using the determined lengths of sessions and a number of sessions, wherein the determining includes comparing location data received from the cellular phone and the stored plurality of times to determine if the likelihood that the cellular phone was at the same location throughout each session of the number of sessions exceeds a threshold: and
 determining an award for each of the members based upon a determined level of participation in the health improvement plan.

15. The method of claim 14, wherein the member one or more of the members can designate, using the mobile computing device, when location information can be sent.

16. The method of claim 14, wherein the geolocation services includes at least one of network location services, a global satellite network, and WiFi location services.

17. The system of claim 1, wherein the application software is further configured to enable the cellular phone for notifying the member if the obtained location and a predetermined location correspond.

18. The system of claim 1, wherein the member can designate, using the cellular phone, when location information can be sent.

* * * * *